(12) United States Patent
Kawashima

(10) Patent No.: US 7,971,627 B2
(45) Date of Patent: Jul. 5, 2011

(54) DEVICE FOR PRODUCING METAL SAMPLE AND PROCESS FOR PRODUCING METAL SAMPLE

(75) Inventor: Yasuji Kawashima, Osaka (JP)

(73) Assignee: Panasonic Corporation, Osaka (JP)

( * ) Notice: Subject to any disclaimer, the term of this patent is extended or adjusted under 35 U.S.C. 154(b) by 716 days.

(21) Appl. No.: 11/996,682

(22) PCT Filed: Jun. 30, 2006

(86) PCT No.: PCT/JP2006/313051
§ 371 (c)(1),
(2), (4) Date: Jan. 24, 2008

(87) PCT Pub. No.: WO2007/013256
PCT Pub. Date: Feb. 1, 2007

(65) Prior Publication Data
US 2010/0282430 A1    Nov. 11, 2010

(30) Foreign Application Priority Data
Jul. 27, 2005   (JP) ................................. 2005-216716

(51) Int. Cl.
*B22D 46/00*   (2006.01)
*G01N 1/12*    (2006.01)

(52) U.S. Cl. ........ 164/4.1; 164/136; 73/863; 73/864.53; 228/103

(58) Field of Classification Search ............... 164/4.1, 164/136; 73/863, 864.53; 228/103
See application file for complete search history.

(56) References Cited

U.S. PATENT DOCUMENTS
| 4,491,412 A * | 1/1985 | Harada et al. ................. 356/36 |
| 4,765,391 A * | 8/1988 | Backerud .................. 164/150.1 |
| 2002/0179693 A1 | 12/2002 | Kawashima et al. |

FOREIGN PATENT DOCUMENTS
| JP | 2-247550 | 10/1990 |
| JP | 2000-121514 | 4/2000 |
| JP | 2002-111194 | 4/2002 |
| JP | 2004-12336 | 1/2004 |
| JP | 2004012336 A * | 1/2004 |

OTHER PUBLICATIONS

International Search Report issued Aug. 8, 2006 in the International (PCT) Application of which the present application is the U.S. National Stage.
Patent Cooperation Treaty (PCT) International Preliminary Report on Patentability, issued Jan. 29, 2008 in International Application No. PCT/JP2006/313051.

* cited by examiner

*Primary Examiner* — Jessica L Ward
*Assistant Examiner* — Devang R Patel
(74) *Attorney, Agent, or Firm* — Wenderoth, Lind & Ponack, L.L.P.

(57) ABSTRACT

A process and a device for easily and rapidly producing a metal sample for analysis for determining the content of impurities in a molten metal with high accuracy. More particularly, according to the metal sample production process, a metal sample for high accuracy analysis is produced by solidifying a collected molten metal without segregating impurities contained in a molten metal, by rapidly cooling a collected molten metal using a metal sample production device having a thin-walled mold having a thin sample collection space for collecting a molten metal, and an opening/closing operation part with which the mold can be freely opened/closed.

1 Claim, 24 Drawing Sheets

Fig. 1
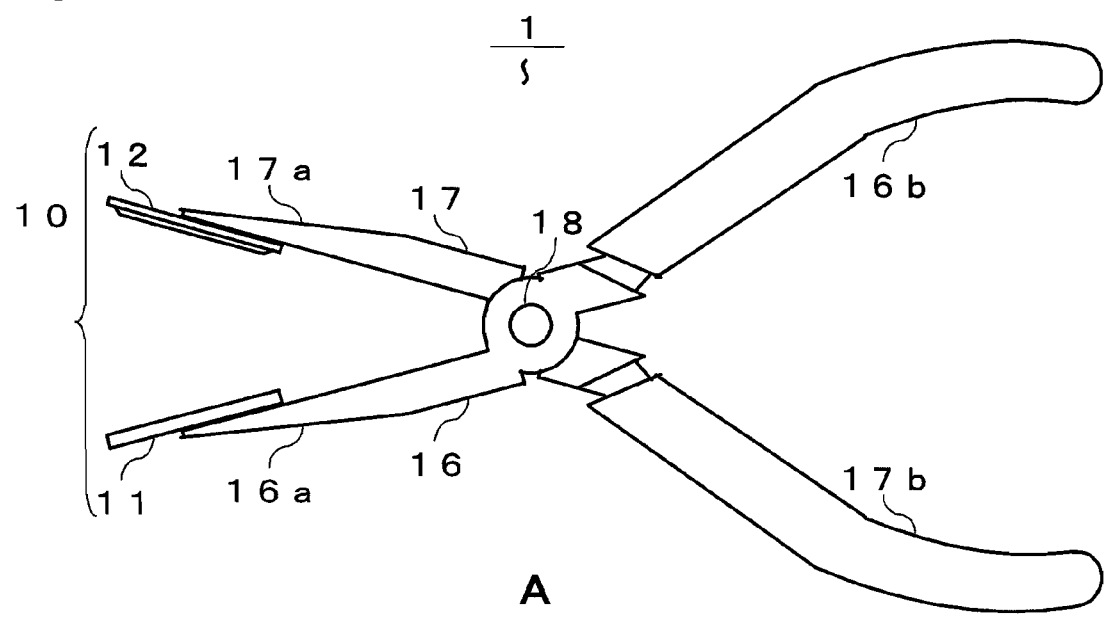
A
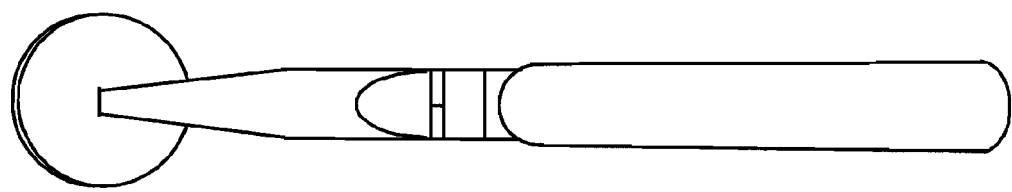
B

Fig. 2
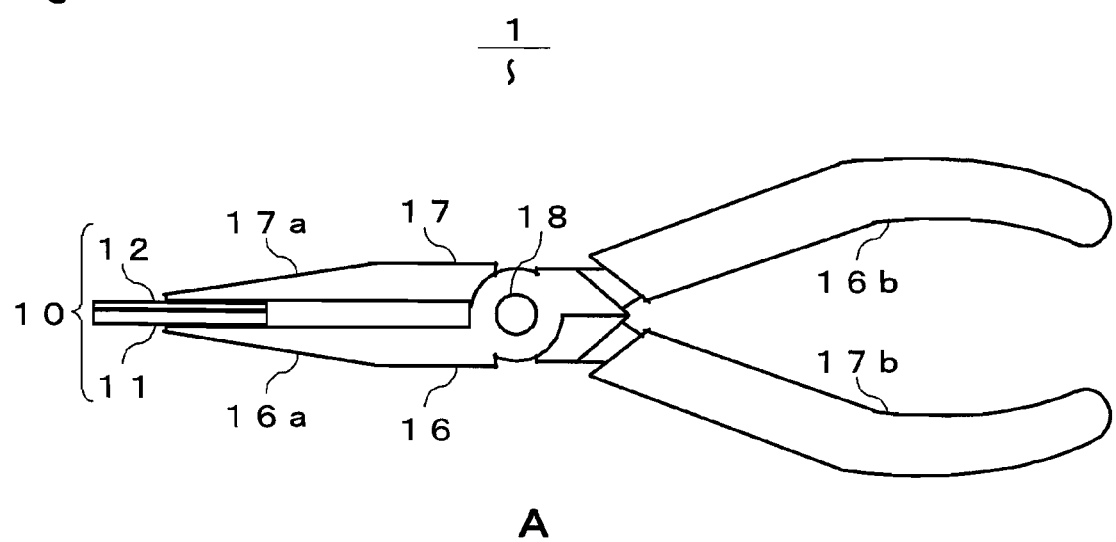
A
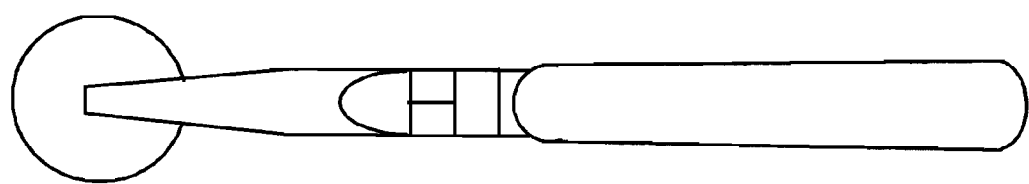
B

Fig. 4
A
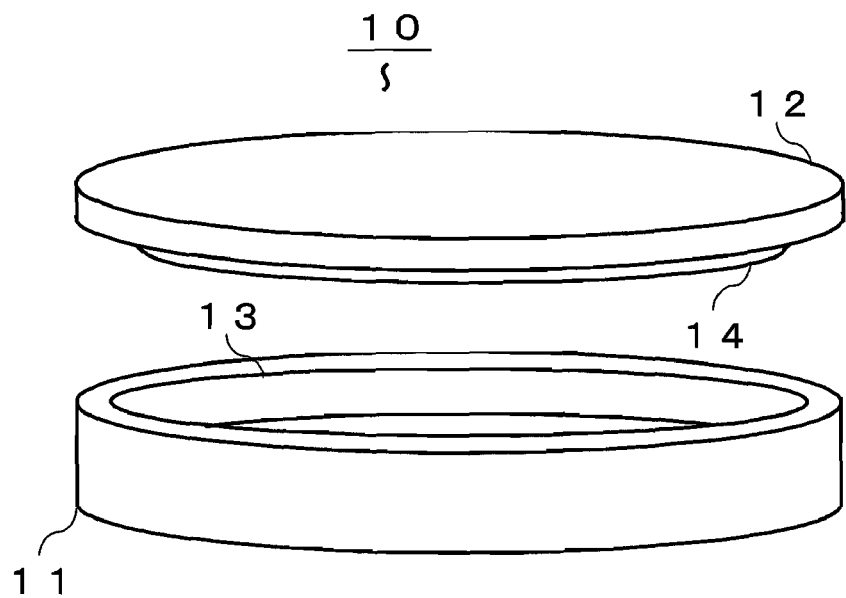
B
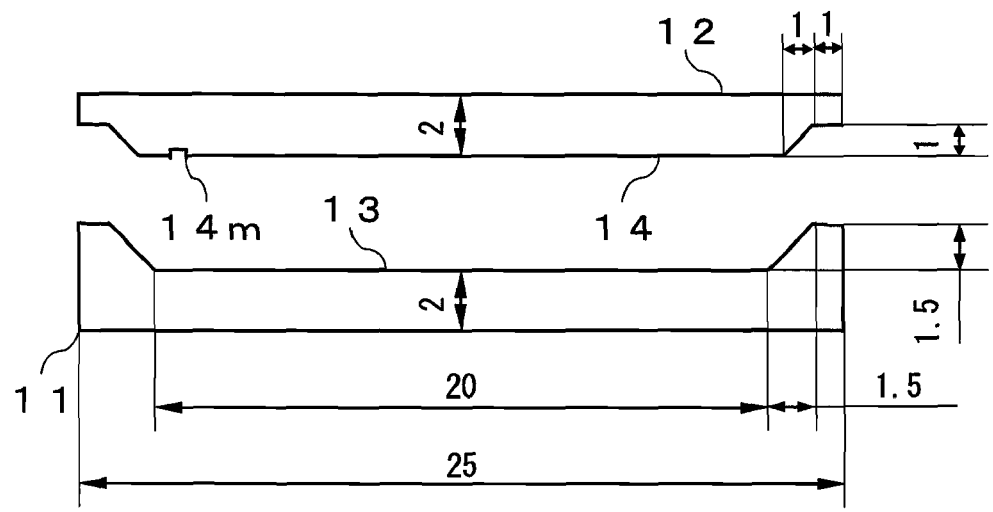
C
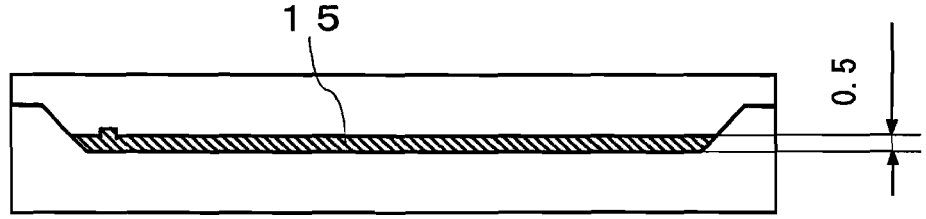

Fig. 5
A
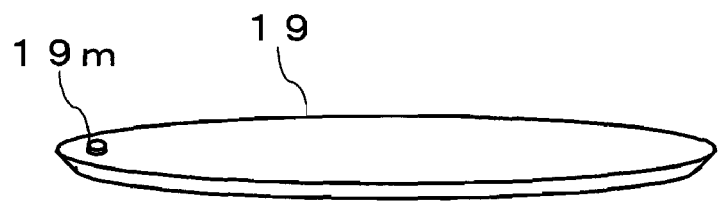
B
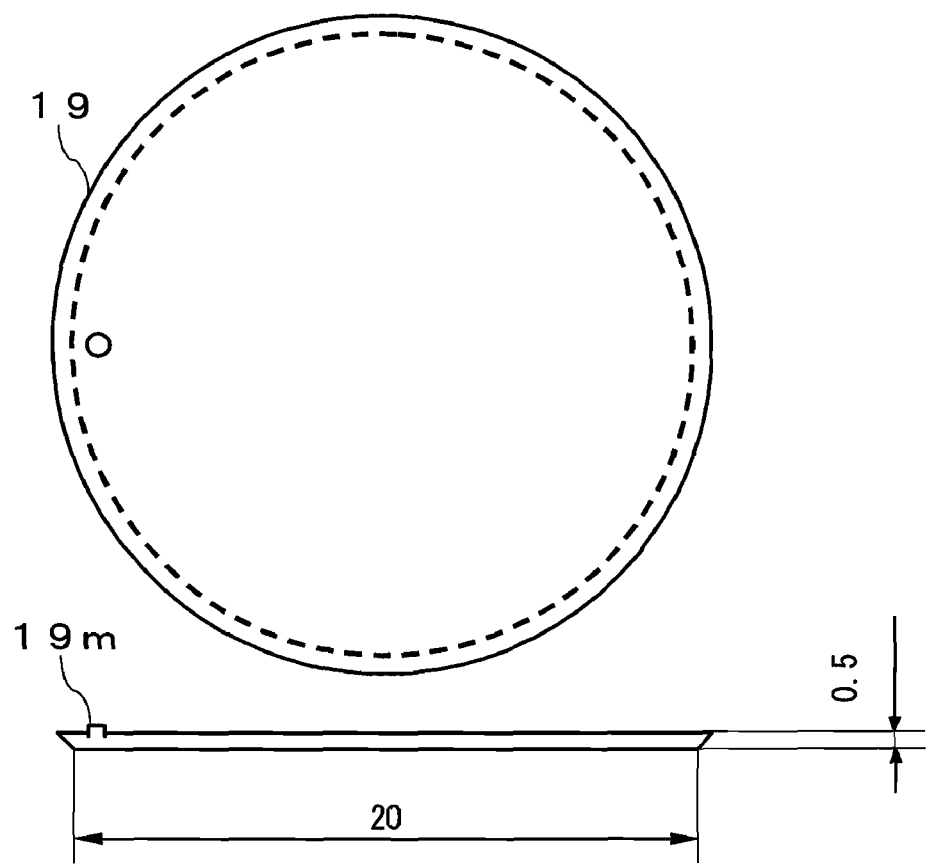

Fig. 6
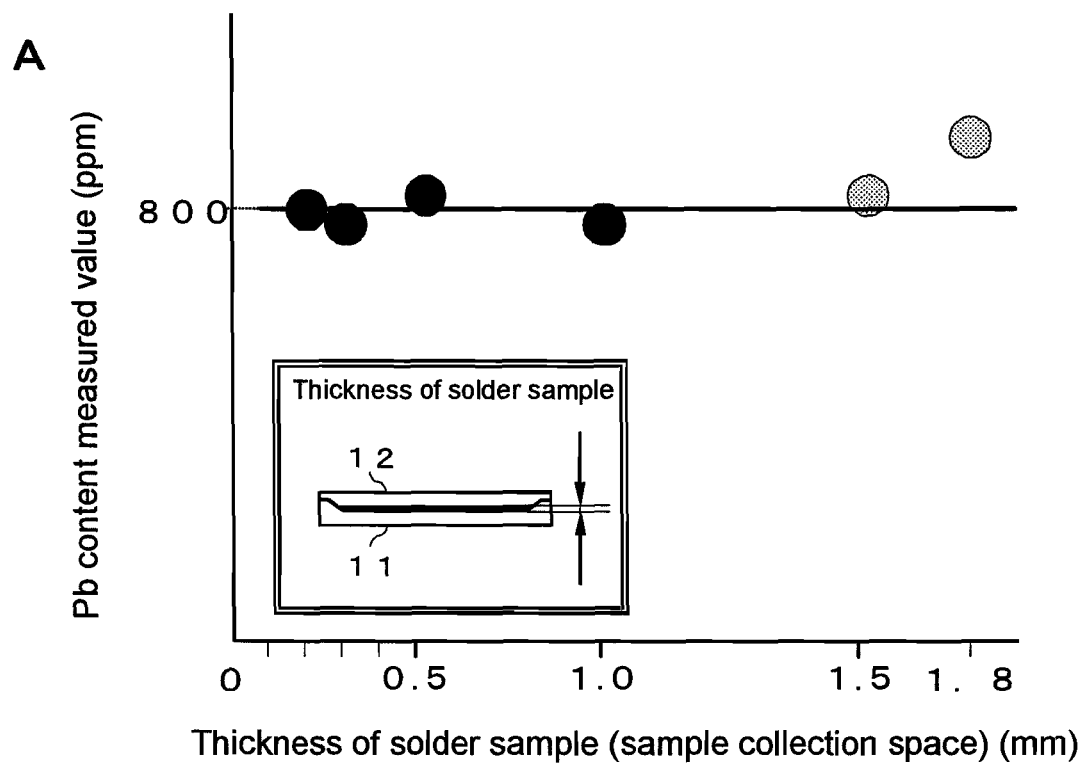
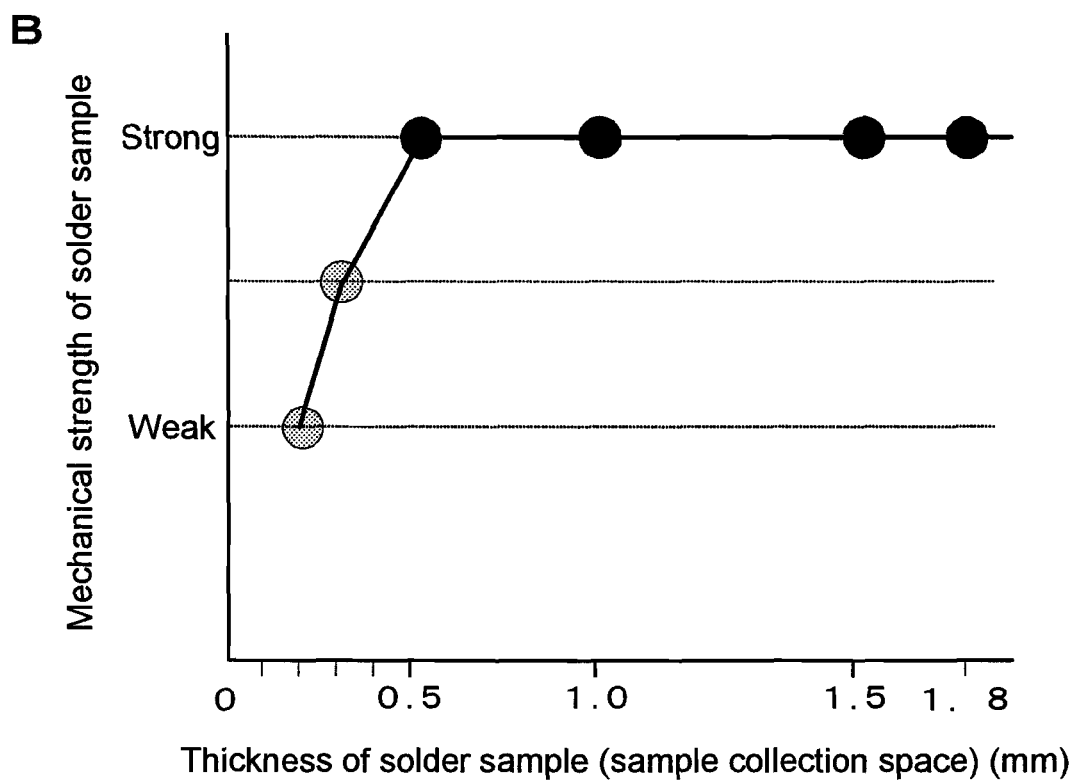

Fig. 7
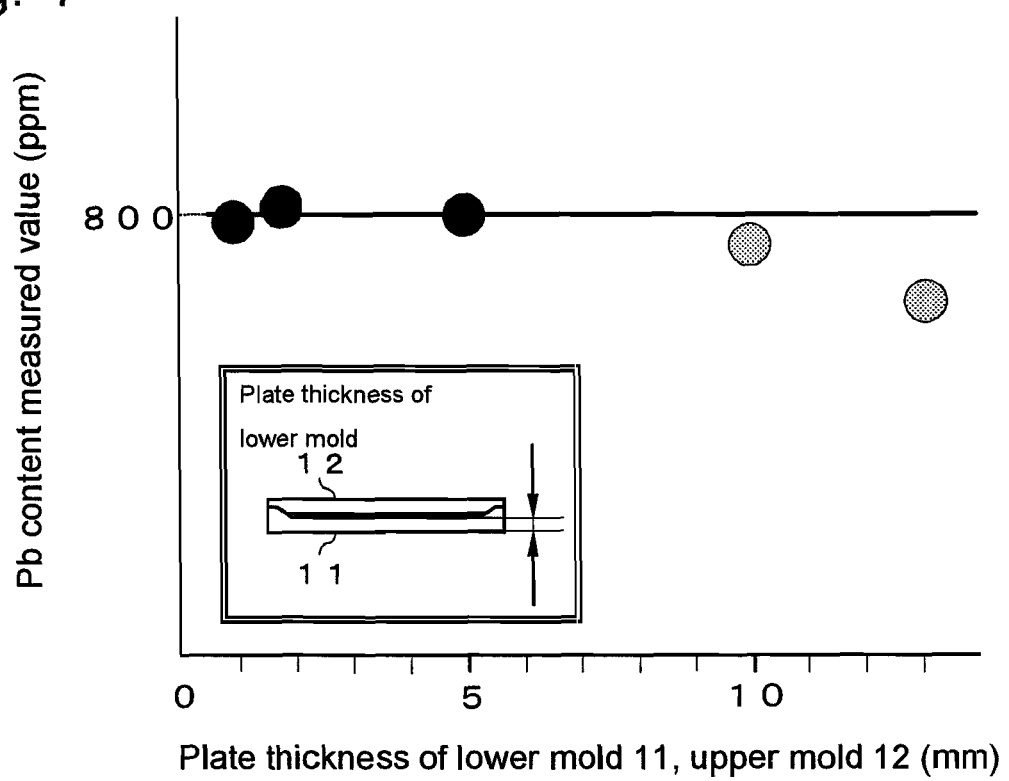
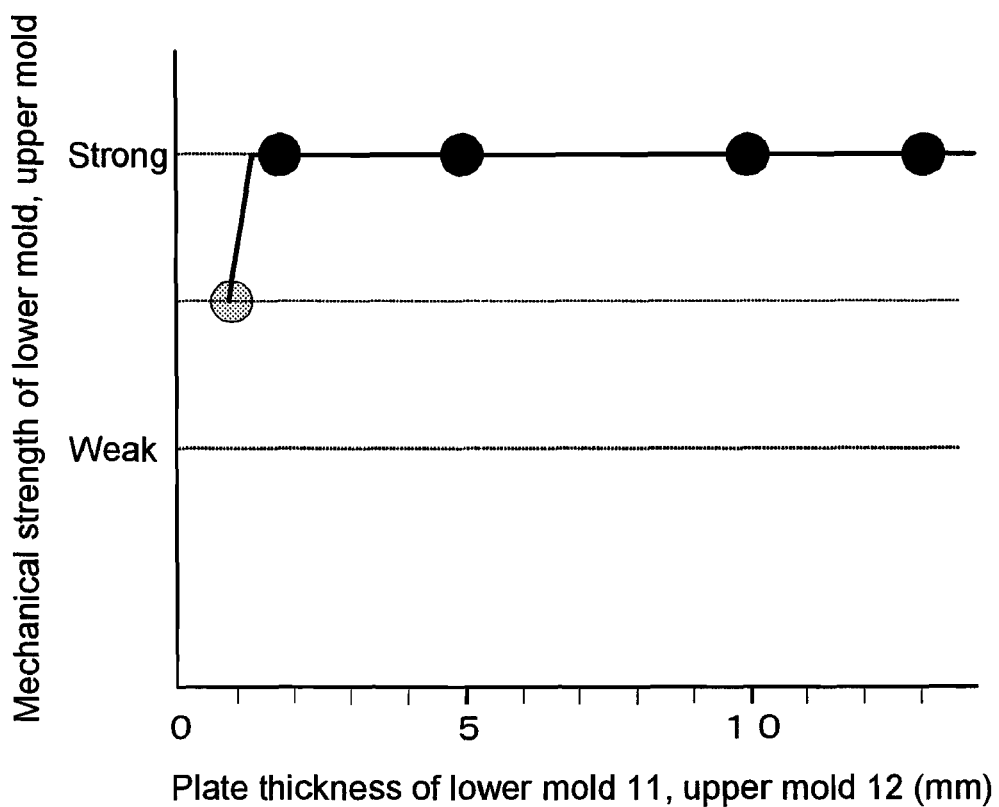

Fig. 11
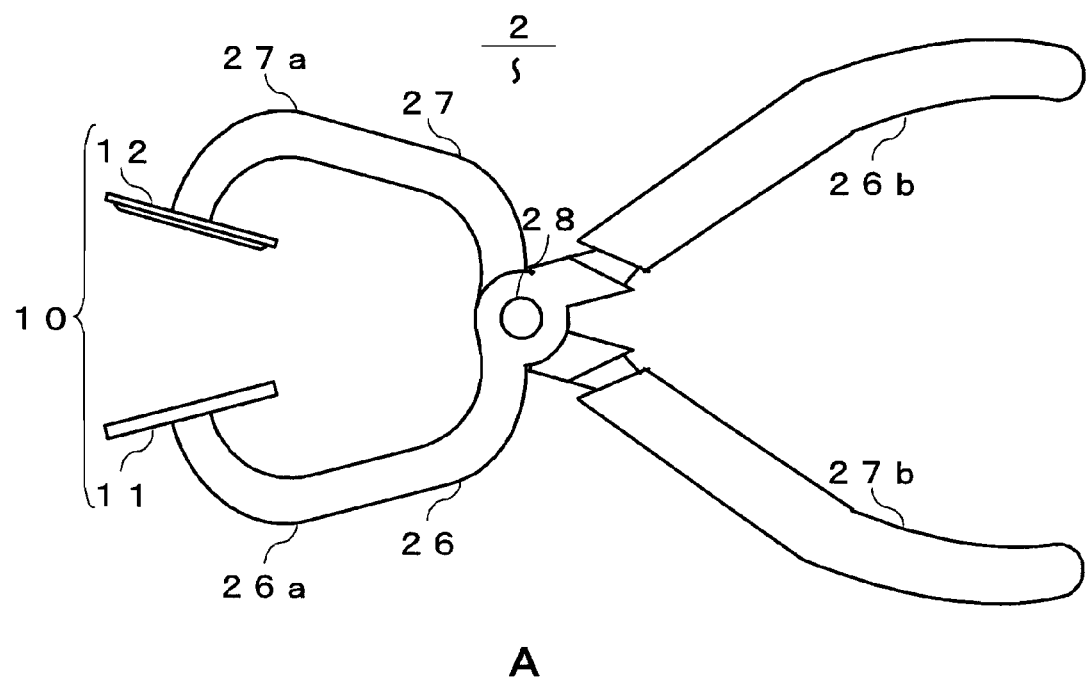
A
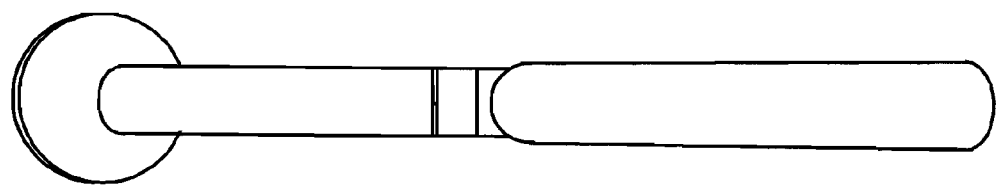
B

Fig. 12
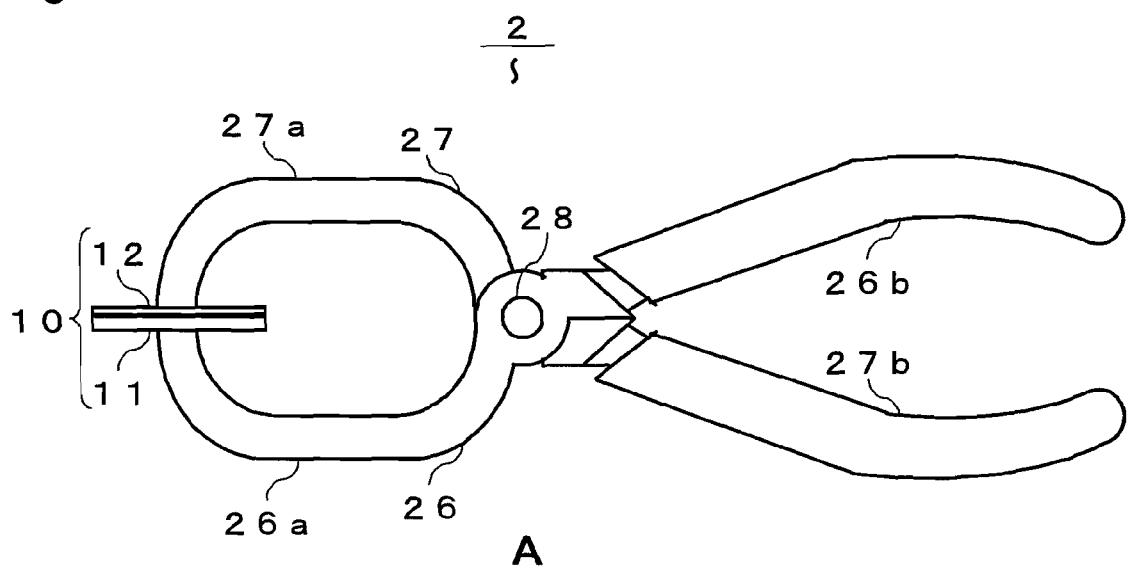
A
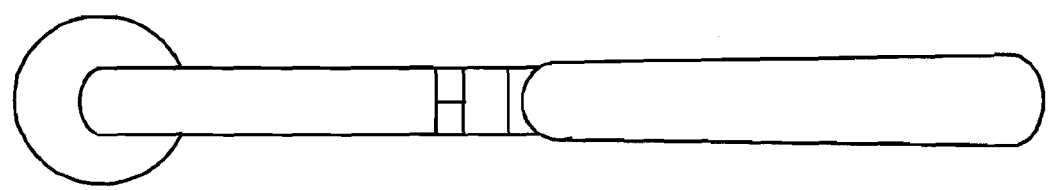
B

Fig. 13
A
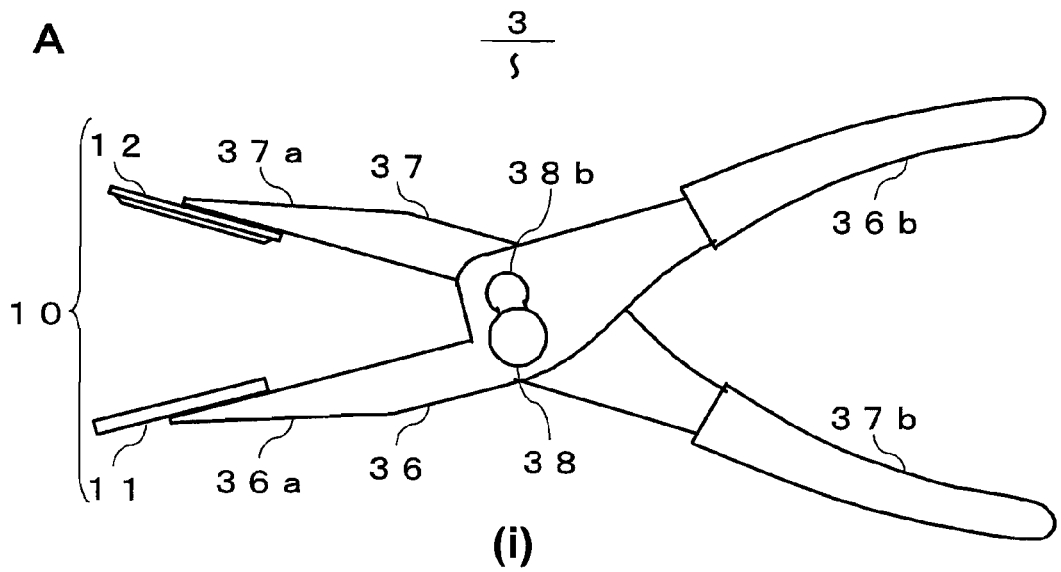
(i)
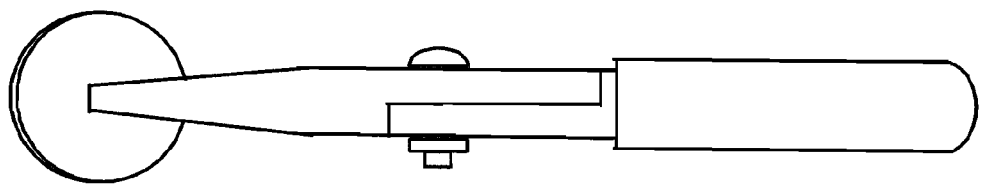
(ii)
B
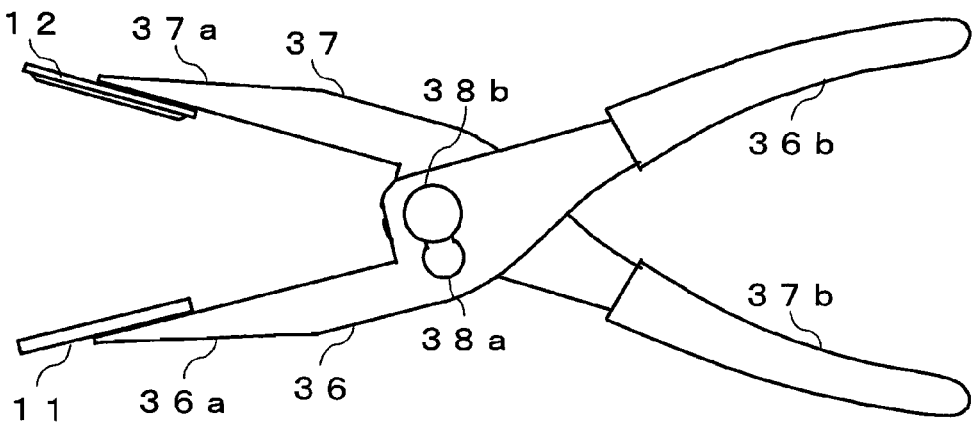

Fig. 14
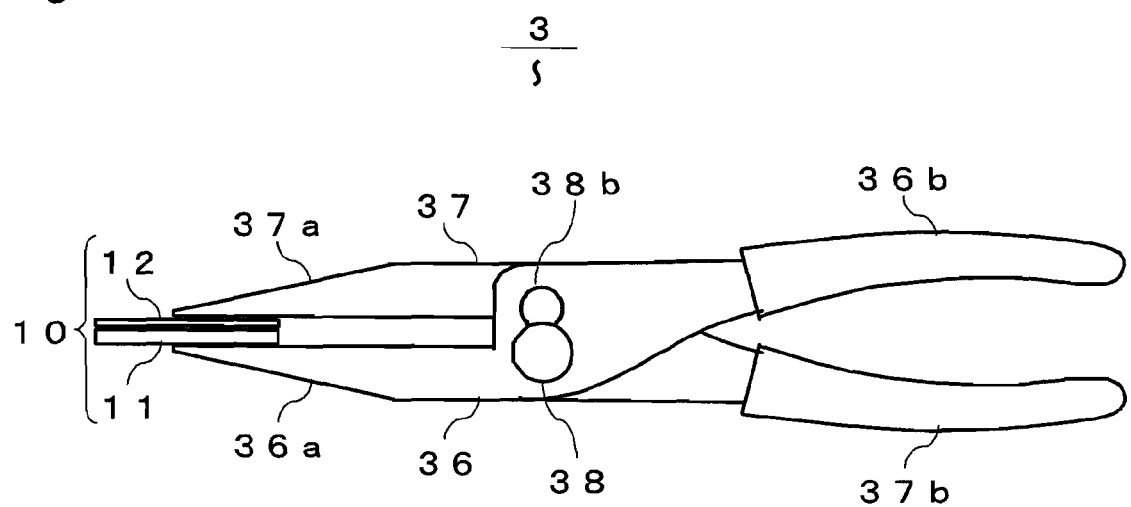
A
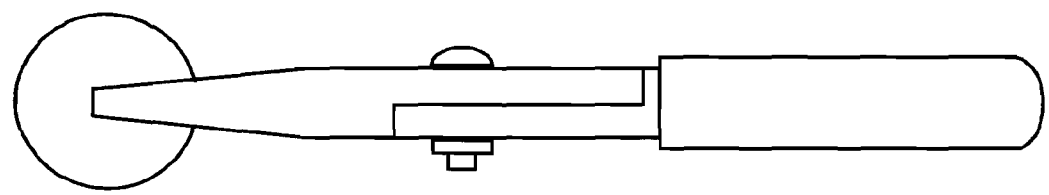
B

Fig. 17
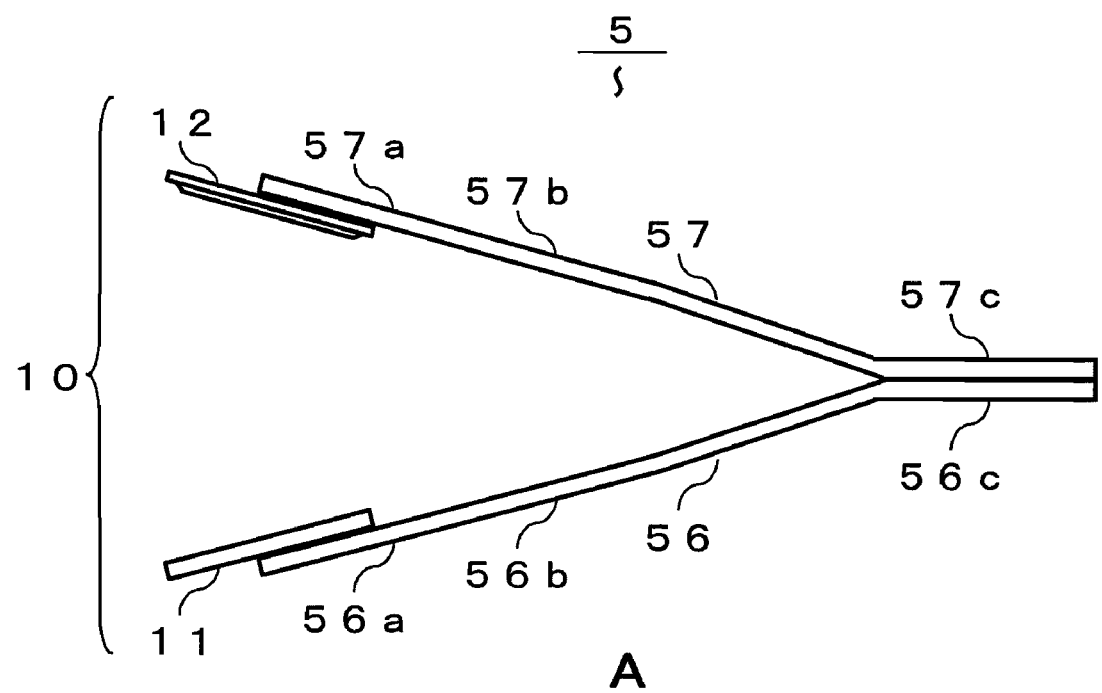
A
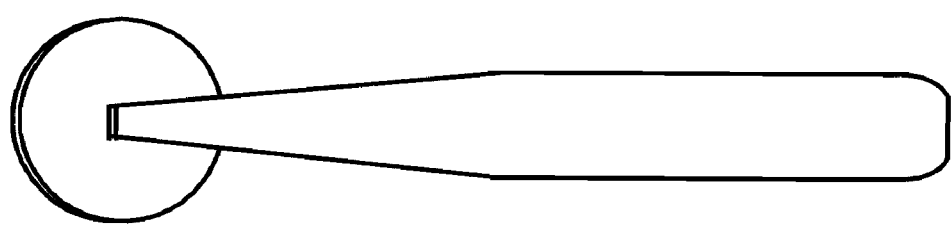
B

Fig. 21
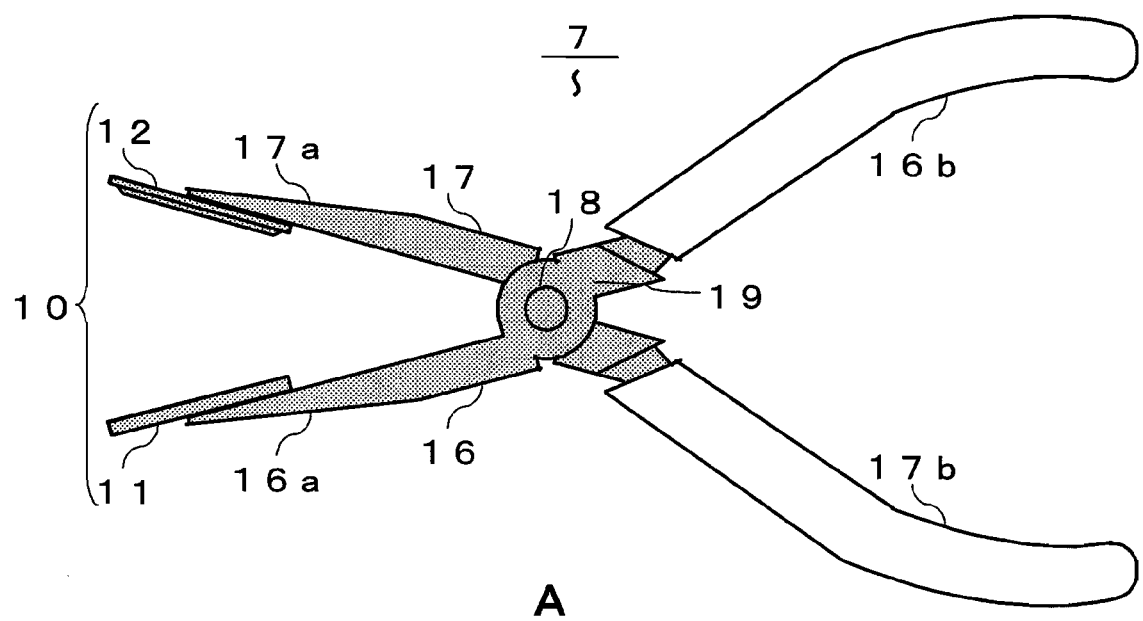
A
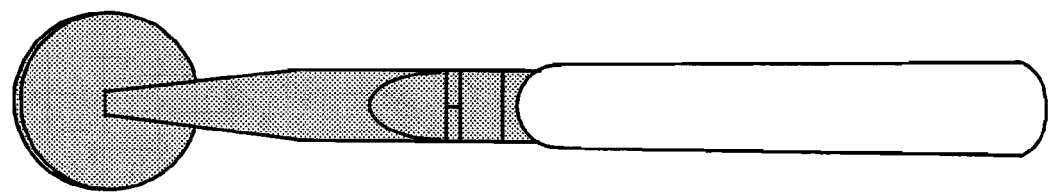
B

FIG. 23 (PRIOR ART)
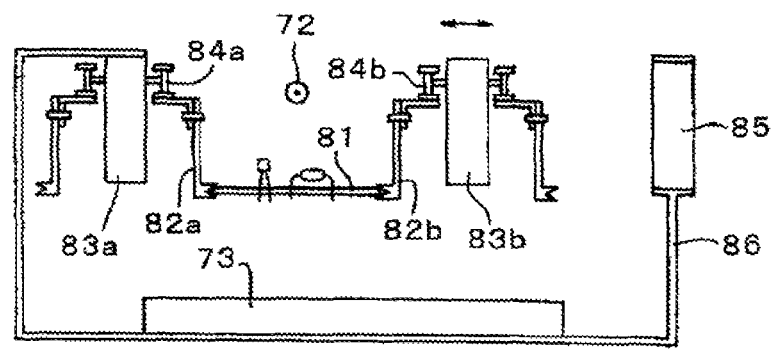
FIG. 24 (PRIOR ART)
A
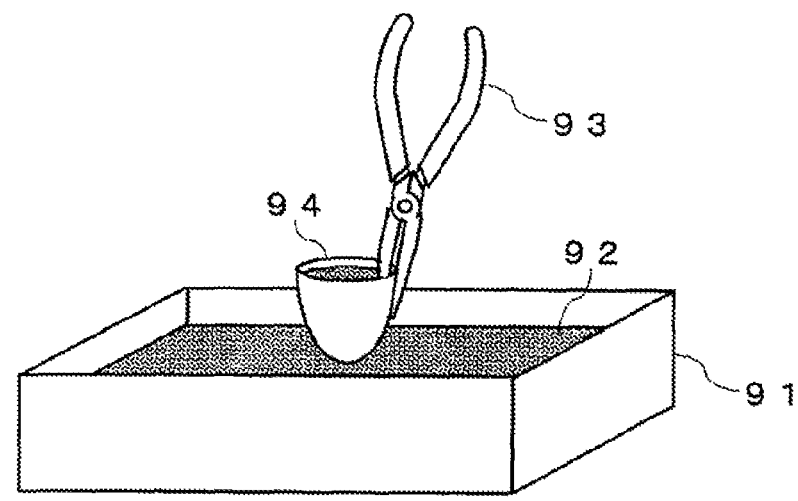
B
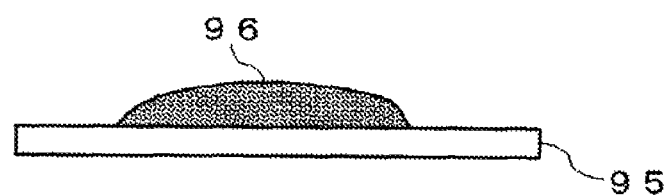

DEVICE FOR PRODUCING METAL SAMPLE AND PROCESS FOR PRODUCING METAL SAMPLE

BACKGROUND OF THE INVENTION

1. Technical Field

The present invention relates to a device and a process for collecting a sample for analysis to be used for determining the content of impurities in a metal, particularly a solder easily, rapidly and with high accuracy.

2. Description of the Related Art

Previously, as one of methods of connecting an electronic part to a substrate in manufacturing an electronic circuit substrate, a flow soldering method of using a molten solder material in a form of a jet has been known. This flow soldering method includes generally a flux coating step of coating a substrate with a flux, a pre-heating step of heating the substrate in advance, and a solder material supplying step of contacting the substrate with a jet consisting of a solder material to supply the solder material to the substrate. The previous general flow soldering method will be explained with reference to drawings below. FIG. 22 is a schematic cross-sectional view of the previous flow soldering device. FIG. 23 is a cross-sectional view along with a X'-X' line of FIG. 22.

First, a flux is supplied to a substrate such as a printed board on which electronic parts such as a through-hole insertion part are properly disposed at predetermined positions by the known method, using a flux supplying means (now shown), thereby, an underside of the substrate is coated with a flux. The flux usually contains an active component such as rosin (resin component) and a solvent such as isopropyl alcohol, and such the flux coating step of coating the substrate with the flux is performed for the purpose of removing an oxidized film (natural oxidized film) which is unavoidably formed on a land (i.e. a part to which a solder material is to be supplied) formed on the substrate, thereby, making wetting spreading of a solder material on a land surface better. As the flux supplying means, a spray fuxer for spraying a misty flux to the substrate, or an expansion fluxer for contacting a foamy flux with the substrate can be used. Such the flux supplying means may be constructed separately from a flow soldering apparatus, or may be integrally incorporated into the interior of a flow soldering apparatus 70.

The substrate coated with a flux as described above is supplied to the flow soldering apparatus 70 of FIG. 22 through an inlet part 71. The substrate 81 is mechanically conveyed in the interior of the apparatus 70 (along with a conveyance line shown with a dotted line in FIG. 22) at constant rate in a direction of an arrow 72. More particularly, conveyance of the substrate 81 is performed by mechanically transferring conveyance claws 82a and 82b holding the substrate 81 at their both ends in a conveyance direction of an arrow 72 as shown in FIG. 23. Herein, conveyance claws 82a and 82b are connected to chains 84a and 84b, respectively, and are roated about conveyer frames 83a and 83b extending from the inlet part 71 to an outlet part 79 shown in FIG. 22 in a plane parallel with a main plane of the substrate 81, respectively. The conveyer frame 83a is a fixed conveyer frame on a standard side, and the conveyer frame 83b is a conveyer frame, on a width adjustment side, which can be slided in a direction vertical to a conveyance direction 72, and parallel with the fixed conveyer frame 83a (i.e. to the left and to the right in a paper plane of FIG. 23).

The substrate 81 which is conveyed in the interior of the apparatus 70 from the inlet part 71 to the outlet part 79 like this is first heated with a pre-heater 73 situated below the substrate 81, such as a far infrared-ray heater. This pre-heating step by heating is performed for heating the substrate 81 in advance prior to supply of a solder material 74 to the substrate 81 to decrease a temperature gradient in an upper and lower direction of the substrate to raise a temperature of a substrate body, for vaporizing an unnecessary solvent component in a flux coated on the substrate 81 by the flux coating step, and for shortening a wetting time (a necessary time from contact of a solder material with a material to be connected (a land in this case) to wetting initiation). Generally, as shown in FIG. 23, the pre-heater 73 has an upper end connected to the fixed conveyer frame 83a and a fixed frame 85, is disposed on a bottom of a groove structure (or a support) 86 having an opening at its upper part, and is disposed below a conveyance line of the substrate 81, and heats the substrate 81 from the same side as a side to which the solder material is supplied, that is, from a lower side of the substrate 81, in a subsequent solder material supplying step.

Subsequently, the substrate 81 is conveyed to above a solder material supplying means 76 including a solder tank 75 charged with a solder material 74 which has been molten by heating in advance, and contanted with a primary jet 77 and a secondary jet 78 consisting of the solder material 74 on a side of an underside of the substrate 81, thereby, the solder material 74 is supplied to the substrate 81. Thereupon, the solder material 74 is wetted up by capillary phenomenon from a side of an underside from the substrate, in an annular space between an inner wall of a through-hole (not shown) formed in the substrate 81 and a lead (not shown) of a through-hole insertion part which is inserted into a through-hole from an upper side of the substrate 81. Thereafter, the solder material which has been supplied and adhered to the substrate 81 solidifies by a fall in a temperature, and forms a connection part consisting of a solder material, a so-called "fillet".

In this solder material supplying step (or flow soldering step), a primary jet 77 is for covering a wall surface of a through-hole to sufficiently wet a surface of a formed land (and a lead of an electronic part) with the solder material and, when this is insufficient, the solder material is not sufficiently wetted up in an annular space between the through-hole and the lead, and a problem of a so-called "land exposure" arises. And, a secondary jet 78 is for removing a solder material adhered to a region covered with a solder resist to adjust a shape of a fillet and, when this is insufficient, the solder material stays and solidifies over lands to form a so-called "bridge" (this bridge is not desirable because it leads to short of an electronic circuit), or forms a square-shaped projection, being not desirable.

The thus obtained substrate 81 is thereafter taken out through the outlet part 79, thereby, an electronic circuit substrate on which electronic parts are soldered to the substrate 81 by the flow soldering method is manufactured.

In the electronic circuit substrate manufactured as described above, previously, a Sn—Pb-based solder material containing Sn and Pb as a main component, particularly a Sn—Pb eutectic solder has been keen generally used. However, since lead contained in a Sn—Pb-based solder material may result in environmental contamination due to improper waste disposal, as a substitute for a solder material containing lead, a solder material containing no lead, a so-called "lead-free solder material" has been started to be used at an industrial scale.

As the "lead-free solder material", Sn—Cu-based, Sn—Ag—Cu-based, Sn—Ag-based, Sn—Ag—Bi-based, Sn—Ag—Bi—Cu-based, Sn—Sb-based, Sn—Bi-based, Sn—Zn-based, and Sn—Zn—Bi-based materials are started to be studied and put into practice.

As a trend of the world for a lead-free material, particularly in Europe, Directive Concerning Restriction on Certain Hazardous Substances Contained in Electric Electronic Apparatuses(hereinafter, referred to as "RoHS Directive") is planned to be enforced from July, 2006, and use of lead which is one of four certain hazardous substances(lead, mercury, cadmium, hexavalent chromium) is prohibited. That is, it becomes essential to switch from a Sn—Pb-based solder to a lead-free solder.

Further, since RoHS Directive plans that a limit value of the content of certain hazardous substances is 100 ppm for cadmium, and 1000 ppm for lead, mercury and hexavalent chromium, even in the case of a lead-free solder such as Sn—Cu-based, Sn—Ag—Cu-based, Sn—Ag-based, and Sn—Ag—Bi-based ones, it is necessary to regulate and control the content of certain hazardous chemical substances, particularly lead, which may be mixed therein as impurities.

For impurities contained in a sample of a metal material, the content thereof can be determined by energy dispersive fluorescent X-ray analysis. In energy dispersive fluorescent X-ray analysis, a flat surface of a metal sample having a predetermined area is irradiated with primary X-ray, and a characteristic(fluorescent) X-ray spectrum generated from elements present in, a superficial layer up to a depth of 100 μm from a surface is measured, thereby, components of substances contained in a metal sample, and their contents are analyzed. Energy dispersive fluorescent X-ray analysis has a very high sensitivity, and detects a few hundreds ppm of impurities at a measurement error of around ±10 ppm.

As a general metal sample which is subjected to energy dispersive fluorescent X-ray analysis, a flat plate having a constant thickness and a small surface roughness, which was manufactured by rolling procession, is used. However, in a solder material unlike a general metal material such as a steel material, a plate is not manufactured by rolling procession.

Previously, for producing a solder sample for analysis, a solder sample has been produced by scooping up a molten solder 92 heated in a solder tank 91 with a crucible 94 equipped with a pincher 93, and cooling and solidifying it in the crucible 94 as shown in FIG. 24A. or a solder sample 96 for analysis has been produced by transferring a molten solder from the crucible 94 to a metal plate (for example, see JP-A No. 2000-121514).

In addition, a metal sample for analysis in a metal refining process has been produced by a sample producing device 100 in which a mold 101 with a inlet port 102 is provided at its tip, as shown in FIG. 25. First, the mold 101 at a tip of the sample production device 100 is immersed in a molten metal, to flow the molten metal into the mold 101. The mold 101 into which the molten metal has been flown is taken out from the molten metal into the air, and cooled to cool the molten metal in the mold 101, thereby, a metal sample for analysis is produced (for example, JP-A No. 2004-012336).

SUMMARY OF THE INVENTION

In order to determine the content of impurities contained in a solder by energy dispersive fluorescent X-ray analysis with high accuracy, it is necessary to make a measuring surface flat so as not to cause a measurement error upon X-ray irradiation.

Further, a solder must be solidified so that impurities contained in a solder are uniformly dispersed in a solder, in order to obtain the same analysis data not depending on a measurement location. That is, a sample must be produced so that the dispersed state of impurities in a molten solder and the dispersed state of impurities in a metal sample produced by solidifying a collected molten solder become substantially the same. Herein, "the dispersed state of impurities in a molten solder and the dispersed state of impurities in a metal sample produced by solidifying a collected molten solder become substantially the same" refers to the state where impurities dispersed in a molten solder are not segregated during a solidification process to increase a local concentration of impurities in a solid metal sample.

For realizing this state, it is necessary to rapidly cool to solidify a molten solder taken from a solder tank.

However, although the previous process for producing a solder sample can easily and rapidly produce a sample, since a shape and a thickness of a sample are irregular, a solidification rate of a solder sample does not partially become constant, impurities are separated into impurities gathering at a rapid solidification rate place and impurities gathering at a slow solidification rate place, and impurities can not be uniformly dispersed in a sample. As a result, a measurement error of 300 to 800 ppm is generated depending on a measurement location, at determination of the content of impurities. Therefore, the previous process has a problem that it is not suitable for controlling the impurities content with high accuracy in order to respond to RoHS Directive which restricts the impurities content at not higher than 1000 ppm.

In addition, the case where the previous process for producing a metal sample in a metal refining process is used in a solder will be considered. A molten solder in a solder tank has a viscosity, and it is difficult to flow a solder into a sample collecting space through an inlet port of not more than 2.0 mm. In addition, when one tries to forcibly suck a solder as in a syringe, since the situation of solder suction in a sample collection space is not seen in the mold, whether the solder has been sucked or not can not be determined, and a hole generated by the air is formed in a solder sample after solder solidification, in some cases. When such the hole is formed in a place requiring a flat plane at analysis of a sample, analysis with high accuracy becomes impossible.

In addition, when a solder sample is produced in a sample collection space having a thickness of not less than 2 mm, since a rate of cooling a solder is different between a place near the mold and a center of the sample collection space, at a middle place, in a solder sample, between a place near the mold where a solidification rate is rapid and a center of the sample collection space where a solidification rate is slow, impurities are separated into impurities gathering at a rapid solidification place and impurities gathering at a slow solidification place, and impurities can not be uniformly dispersed. As a result, a measurement error of 300 to 800 ppm is generated depending on a measurement location at determination of the content of impurities. Therefore, the previous process has a problem that it is not suitable for collecting the impurities content with high accuracy in order to respond to RoHS Directive which restricts the impurities content at not higher than 1000 ppm.

In addition, when one tries to produce a solder plate as in a metal sample in order to perform measurement with high accuracy, since production of an ingot of a solder alloy, cutting procession of a thin plate, and abrasion work are necessary, this process has a problem that long time and labor are required.

The present invention solves the aforementioned previous problems, and an object thereof is to provide a process and a device for easily and rapidly producing a sample for analysis for determining the content of impurities contained in a molten metal, particularly a molten solder with high accuracy, by energy dispersive fluorescent X-ray analysis.

In order to solve the aforementioned previous problems, the device for sample production of the present invention has a thin-walled mold having a thin sample collection space for collecting a molten metal, and an opening/closing operation part with which the mold can be freely opened/closed.

The present essential feature enables to immerse a mold in a molten metal, collect a molten metal into a thin sample collection space, and rapidly cool the molten metal to produce a thin metal sample.

In addition, the sample production devide of the present invention is such that a mold and an opening/closing operation part are constructed of a material having low solderability and, further, an arm interval at an opening/closing operation part is set to be not smaller than a predetermined value, thereby, a solder is hardly adhered to a sample production device and, at the same time, an opening/closing operation is not prevented even when a solder in adhered thereto.

According to the device and the process for collecting a sample for analysis for determining the content of impurities contained in a solder easily, rapidly and with high accuracy of the present invention, a solder sample for energy dispersive fluorescent X-ray analysis can be easily and rapidly collected, and whether four certain hazardous chemical substances (lead, mercury, cadmium, hexavalent chromium) designated by RoHS Directive are contained as impurities or not can be measured with high accuracy.

BRIEF DESCRIPTION OF THE DRAWINGS

[FIG. 1] A structural view when a mold of a sample production device 1 in accordance with an aspect 1 of the present invention is opened. A: front view, B: side view.

[FIG. 2] A structural view when a mold of a sample production device 1 in accordance with an aspect 1 of the present invention is closed; A: front view, B: side view.

[FIG. 4] A structural view of a mold of a sample production device in accordance with an aspect 1 of the present invention; A: a perspective in which a mold is opened, B: a cross sectional view in which a mold is opened, C: a cross-sectional view in which a mold is closed.

[FIG. 5] A schematic view of a sample produced by a sample production device in accordance with an aspect 1 of the present invention; A: perspective, B: bifacial view.

[FIG. 6] A view showing a relationship between a thickness of a solder sample collected with a sample production device in accordance with an aspect 1 of the present invention; A: a relationship view of the Pb content; B: a relationship view of a mechanical strength of a solder sample.

[FIG. 7] A view showing a relationship between a plate thickness of a lower mold and an upper mold of a sample production device in accordance with an aspect 1 of the present invention; A: a relationship view of the Pb content, B: a relationship view of a mechanical strength of a mold.

[FIG. 11] A structural view when a mold of a sample production device 2 in accordance with an aspect 1 of the present invention is opened; A: front view, B: side view.

[FIG. 12] A structural view when a mold of a sample production device 2 in accordance with an aspect 1 of the present invention is closed; A: front view, B: side view.

[FIG. 13] A structural view when a mold of a sample production device 3 in accordance with an aspect 1 of the present invention is opened; A: a structural view when a rotation supporting point is 38$a$; (i): front view, (ii): side view, B: a structural view when a rotation supporting point is 38$b$.

[FIG. 14] A structural view when a mold of a sample production device 3 in accordance with an aspect 1 of the present invention is closed; A: front view; B: side view.

[FIG. 17] A structural view when a mold of a sample production device 5 in accordance with an aspect 1 of the present invention is opened; A: front view; B: side view.

[FIG. 21] A structure of a sample production device 7 in accordance with an aspect 2 of the present invention; A: front view, B: side view.

[FIG. 23] A cross-sectional view along with a X'-X' line of FIG. 22.

[FIG. 24] A schematic view of the previous sample production process; A: a view in which a molten solder is scooped with a crucible, B: a view in which a solder is spread on a metal plate.

DETAILED DESCRIPTION OF THE INVENTION

Figure 3:
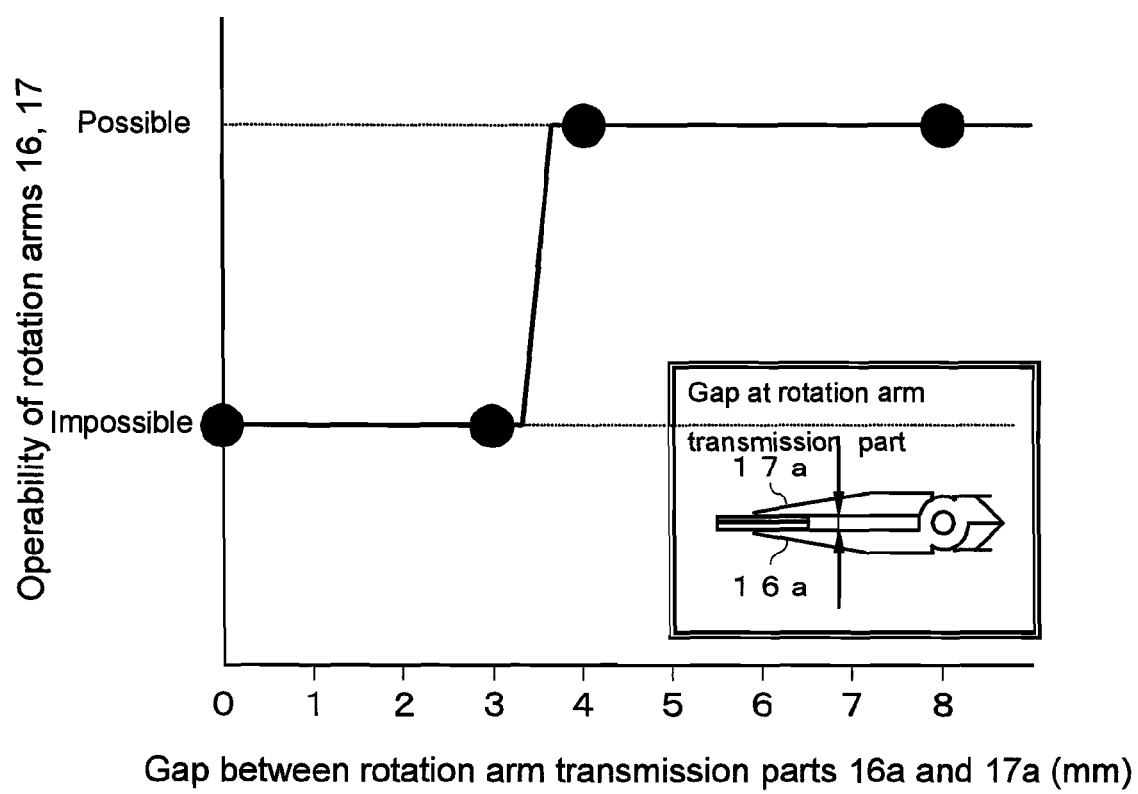
[FIG. 3] A view showing a relationship between a gap of a rotation arm transmission part of a sample production device in accordance with an aspect 1 of the present invention, and operability.

Preferred embodiments of the invention will be explained below with reference to the drawings.

(Aspect 1)

A. Device for Producing Solder Sample from Molten Solder

FIG. 1 and FIG. 2 are a fundamental structural view of a sample production device 1 in accordance with an aspect 1 of the present invention. The sample production device of FIG. 1 consists of a mold 10 which is separated into a lower mold 11 and an upper mold 12, a rotation arm 16 having a rotation arm transmission part 16$a$ and a rotation arm acting force inputting part 16$b$, which fix and support the lower mold 11, and a rotation arm 17 having a rotation arm transmission part 17$a$ and a rotation arm acting force inputting part 17$b$, which fix and support the upper mold 12, as an opening/closing operation part with which the mold 10 is opened/closed, and a rotation supporting point 18 which is to be a rotation center for the rotation arm 16 and the rotation arm 17.

FIG. 1 shows the state where the mold 10 is opened in the sample production device 1, that is, the state where the lower mold 11 and the upper mold 12 are separated. FIG. 2 shows the state where the mold 10 is closed in the sample production device 1, that is, the state where the upper mold 12 is fitted in the lower mold 11.

When an acting force is inputted into one or both of the rotation arm acting force inputting parts 16b and 17b in such a direction that the rotation arm acting force inputting part 16b and the rotation arm acting force inputting part 17b are approaching to each other, in the state where the mold 10 is opened in the sample production device 1 as shown in FIG. 1, one or both of the rotation arm 16 and the rotation arm 17 is (are) rotated about the rotation supporting point 18, and the rotation arm transmission parts 16a and 16b achieve the state where the upper mold 12 is fitted in the lower mold 11, that is, the state where the mold 10 is closed in the sample production device 1 as shown in FIG. 2.

Conversely, when an acting force is inputted into one or both of rotation arm acting force inputting parts 16b and 17b in such a direction that the rotation arm acting force inputting part 16b and the rotation arm acting force inputting part 17b move away from each other, in the state where the mold 10 is closed as shown in FIG. 2, one or both of the rotation arm 16 and the rotation arm 17 is (are) rotated about the rotation supporting point 18, and the rotation arm transmission parts 16a and 17b achieve the state where the lower mold 11 and the upper mold 12 are separated, that is, the state where the mold 10 is opened in the sample production device 1 as shown in FIG. 1.

The rotation arm 16 is constructed of the rotation arm transmission part 16a having a tip with the lower mold 11 fixed thereto, and the rotation arm acting force inputting part 16b disposed in point symmetry with the rotation arm transmission part 16a about the rotation supporting point 18. When an acting force is inputted into the rotation arm acting force inputting part 16b, the acting force is transmitted to the rotation arm transmission part 16a about the rotation supporting point 18, making the lower mold 11 approach to or move away from the upper mold 12.

Similarly, the rotation arm 17 is constructed of the rotation arm transmission part 17a having a tip with the upper mold 12 fixed thereto, and the rotation arm acting force inputting part 17b disposed in point symmetry with the rotation transmission part 17a about the rotation supporting part 18. When an acting force is inputted into the rotation arm acting force inputting part 17b, the acting force is transmitted to the rotation arm transmission part 17a about the rotation supporting point 18, making the upper mold 12 approach to or move away from the lower mold 11.

The rotation supporting point 18 penetrates through both the rotation arm 16 and the rotation arm 17 to connect them, and is positioned as a rotation center for both arms.

For producing a solder sample, the mold 10 is immersed into a molten solder in a solder tank. Thereupon, the rotation arm transmission parts 16a and 17a of rotation arms 16 and 17 are also immersed into a molten solder in a solder tank. Thereupon, since when a solder is adhered to rotation arm transmission parts 16a and 17a, and is solidified, an operation of opening/closing the mold 10 can not be performed, rotation arm transmission parts 16a and 17a are constructed of a material having low solderability so that a solder is adhered thereto with difficulty. As the material having low solderability, a material containing, as a main component, any of steel, stainless, nichrome, aluminum, chromium, titanium, and ceramics can be used. Among them, particularly, steel, stainless and titanium are excellent in corrosion resistance to a solder, and are suitable for a structural material of rotation arms 16 and 17 in the present invention.

As the structural material of rotation arm transmission parts 16a and 17a, a material of suitable quality may be selected in view of a kind, characteristic, and a temperature of a molten metal and, further, contamination-corrosion with a molten metal, the material cost and the like. According to the experimental result by the present inventor, in the case where the molten metal is a solder, stainless such as SUS304 and SUS316 is preferable.

In addition, even if rotation arm transmission parts 16a and 17a are constructed of a material having low solderability such as stainless, when rotation arm transmission parts 16a and 17a of the sample production device 1 which is allowed to stand at a normal temperature(around 25° C.) are immersed in a molten solder in a solder tank at 255° C., a solder is adhered around rotation arm transmission parts 16a and 17a, and solidified there due to a difference in a temperature of about 230° C. Thereupon, if a gap between the rotation arm transmission part 16a and the rotation arm transmission part 17a is small, the rotation arm transmission part 16a and the rotation arm transmission part 17a are connected with the solidified solder, preventing an operation of opening/closing the mold 10. Therefore, a gap not smaller than a certain gap is required between the rotation arm transmission part 16a and the rotation arm transmission part 17b, in the state where the mold 10 is closed as shown in FIG. 2.

As shown in FIG. 3, according to the experimental result by the present inventor, when immersed into a molten solder in a solder tank while a gap between the rotation arm transmission part 16a and the rotation arm transmission part 17a was adjusted, the solder was solidified connecting the rotation arm transmission part 16a and the rotation arm transmission part 17a, at a gap of not greater than 3 mm, and the rotation arm transmission part 16a and the rotation arm transmission part 17a could not be operated, thus, an operation of opening/closing the mold 10 could not be performed. At a gap not smaller than 4 mm, the solder was solidified around each of the rotation arm transmission part 16a and the rotation arm transmission part 17a, but the rotation arm transmission, part 16a and the rotation arm transmission part 17b were not connected, therefore, the rotation arm transmission part 16a and the rotation arm transmission part 17a could be operated, and an operation of opening/closing the mold 10 could be performed.

From these things, a gap between the rotation arm transmission part 16a and the rotation arm transmission part 17a was set to be not smaller than 4 mm, in the state where the mold 10 was closed. And, since a thickness of the mold 10 is not smaller than 4 mm as described later, it results in that a gap between the rotation arm transmission part 16a and the rotation arm transmission part 17a may be not smaller than a thickness of the mold 10. From this, rotation arm transmission parts 16a and 17a were constructed to hold the mold 10 from upper and lower sides as shown in FIG. 2.

It is desirable that rotation arm acting force inputting parts 16b and 17b are formed being integrated with rotation arm transmission parts 16a and 17a in order to transmit an acting force to rotation arm transmission parts 16a and 17a, and they are constructed of the same material. Since rotation arm acting force inputting parts 16b and 17b are a site for inputting an acting force for opening/closing-operating the mold 10, by being held with a hand of a user, they are not immersed into a molten solder in a solder tank. Therefore, rotation arm acting force inputting parts 16b and 17b may be used as they are, but it is more desirable that they are covered with a rubber so that a user holds them comfortably.

That is, the sample production device 1 is a pincher-shaped sample production device in which a mold 10 for collecting a solder sample is fixed at its tip, and a gap between a rotation arm transmission part 16a for fixing and supporting a lower mold 11 of a mold 10, and a rotation arm transmission part 17a for fixing and supporting an upper mold 12 is optimized.

Then, a fundamental structure of a mold 10 of the sample production device 1 of the present invention is shown in FIG. 4. The mold 10 is constructed of a lower mold 11 and an upper mold 12 which form a sample collection space 15, for collecting a solder sample for analysis. In the lower mold 11, a collection part 13 which is a concave part for collecting a molten solder is formed. In the upper mold 12, a pushing out part 14 which is a convex part having an equivalent diameter to that of the lower mold 11 and fitting in the collection part 13 of the lower mold 11, is formed.

The mold 10 is constructed so that, when the lower mold 11 and the upper mold 12 are fitted, the pushing out part 14 of the upper mold 12 is fitted in the collection part 13 of the lower mold 11, and a thickness of the sample collection space 15 formed between a bottom of the collection part 13 and an upper surface of the pushing out part 14 becomes 0.3 to 1.5 mm. A thickness of the sample collection space 15 is to be a thickness of a solder sample 19 after a solder is solidified.

A perspective of the solder sample 19 formed in the sample collection space 15 of the mold 10 shown in FIG. 4 is shown in FIG. 5A, and a bifacial view thereof is shown in FIG. 5B. The solder sample 19 has a diameter of 20 mm and a thickness of 0.5 mm, thus, has the same shape and dimension as those of the sample collection space 15. In the solder sample 19, a surface which has been contacted with a bottom of a concave part of the collection part 13 of the lower mold 11 is to be a measurement surface upon energy dispersive fluorescent X-ray analysis, and is to be a surface side of a solder sample. Conversely, a surface which has been contacted with an upper surface of the pushing out part 14 of the upper mold 12 is to be a back side of the solder sample.

A thickness of the sample collection space 15, that is, a thickness of the solder sample 19 influences on a solidification time of a molten solder and, when a thickness of the sample collection space 15 is increased, impurities components in a solder are easily segregated due to delayment of a time until solidification of a molten solder. Therefore, in order to uniformly disperse and solidify impurities in a solder sample 19, a thickness of a solder sample 19 is suitably smaller so as to rapidly cool and solidify a molten solder.

FIG. 6A is a view showing a relationship between a thickness of the solder sample 19 and the content of Pb which is an impurity in the solder sample 19. In this experiment, a standard solder having the Pb content of 800 ppm was used.

As shown in FIG. 6A, little difference is seen in a measured value of the Pb content by energy dispersive fluorescent X-ray analysis, at a thickness of the solder sample 19 (sample collection space 15) of 0.2, 0.3, 0.5, 1.0 and 1.5 mm, and the Pb content is detected with high accuracy (800 ppm±30 ppm).

However, when the solder sample 19 is 1.5 mm, a white surface layer appeared on a surface on a back side of the solder sample 19, and symptom showing that a solidification rate is delayed than a surface side of the solder sample 19 began to appear. Further, when a thickness of the solder sample 19 is greater than 1.8 mm, a whole back surface of the solder sample 19 became a white surface layer, the content of Pb was detected to be 910 ppm, and an error was seen in data. Therefore, it is necessary that a thickness of the solder sample 19 is not greater than 1.5 mm.

Conversely, when a thickness of the sample collection space 15 is too small, a mechanical strength of a sample is reduced. And, when a force is applied too much in handling at removal of the solder sample 19, and setting of the solder sample 19 on a sample bed for energy dispersive fluorescent X-ray analysis, the solder sample 19 is cracked or bended. As shown in FIG. 6B, when a thickness of the solder sample 19 (sample collection space 15) is 0.2 mm, the sample was greatly deformed, and measurement became very difficult, at removal of the resulting solder sample from the mold 10. When a thickness of the solder sample 19 (sample collection space 15) was 0.3 mm, application of a great force deformed the sample, but measurement was possible. Further, when a thickness of the sample collection space 15 was not smaller than 0.5, the sample was not deformed at normal handling, and measurement was not influenced at all.

Further, in energy dispersive fluorescent X-ray analysis, since fluorescent X-ray spectra generated from elements present in a superficial layer from a surface to a depth of 0.1 mm (100 μm) of the solder sample 19 are measured, when the sample it too thin, analysis accuracy is adversely influenced. Therefore, it is necessary that the solder sample 19 has a thickness of not smaller than 0.3 mm.

Hence, a thickness of the sample collection space 15, that is, a thickness of the solder sample 19 is suitably 0.3 to 1.5 mm. Particularly, in a range of 0.5 to 1.0 mm, uniform distribution of impurities and a mechanical strength were stable. The present invention will be explained, letting a representative value of a thickness of the sample collection space 15 to be 0.5 mm.

In addition, a planar shape of the sample collection space 15 is not particularly limited, but a circle shape or an elliptic shape is preferable in that a solidification rate is generally maintained constant over a whole sample in rapid cooling, and a uniform solidified tissue is acquired, and in that the solder sample 19 is easily removed from the mold.

A size of a planar shape of the sample collection space 15 is determined by a sample bed of an energy dispersive fluorescent X-ray analysis apparatus. Since measurement is performed on a sample bed of a currently commercially available energy dispersive fluorescent X-ray analysis apparatus, a sample having a flat plane having a diameter of not smaller than 10 mm is usually necessary. Therefore, the sample collection space 15 is made to be a circle or, an ellipse having a diameter of 10 to 30 mm.

A depth of the collection part 13 of the lower mold 11 is made to be a depth corresponding to a sum of a thickness of the solder sample 19 and a thickness of the pushing out part 14 of the upper mold 12. For example, in FIG. 4, since a thickness of the solder sample 19 is 0.5 mm, and a thickness of the pushing out part 14 is 1.0 mm, then a depth of the collection part 13 is 1.5 mm.

Thereby, it becomes possible to fill a molten solder into the sample collection space 15 by collecting a molten solder having a volume larger than a volume of the sample collection space 15 into the collection part 13 of the lower mold 11, and pushing out an extra solder with the pushing out part 14 of the upper mold 12. Further, a bottom of the collection part 13 has a flat surface having a surface not smaller than a certain area so that a flat surface having an area larger than an area required for energy dispersive fluorescent X-ray analysis can be maintained so as to be used as a measurement surface for the collected solder sample 19.

The pushing out part 14 of the upper mold 12 has a thickness of 0.5 to 1.5 mm in order to push out an extra solder at the collection part 13 when the pushing out part 14 is fitted into the collection part 13 of the lower mold 11. For example, in FIG. 4, a thickness of the pushing out part 14 of the upper mold 12 is 1.0 mm. Thereby, a thickness of the sample collection space 15 formed by fitting of the collection part 13 of the lower mold 11 and the upper mold 12 becomes 0.5 mm when a depth of the collection part 13 is 1.5 mm, and is a suitable thickness for uniformly solidifying the solder sample 19.

Further, a surface of the pushing out part 14 has a flat surface having an area not smaller than a certain area so that a surface of the collected sample becomes a flat surface having an area not smaller than a predetermined area.

In addition, a circular concave part 14*m* for marking is provided in the pushing out part 14 of the upper mold 12, for indicating a back surface of the solder sample 19. The concave part 14*m* for marking is positioned around an outer periphery of the pushing out part 14 remote from a measurement part of the solder sample 19 so that measurement of components of the solder sample 19 is not adversely influenced. Thereby, when the solder sample 19 is removed from the mold 10, a convex marking is formed around an outer periphery of a back surface of the solder sample 19.

The mold 10 is constructed of a material having low solderability so that the solder sample 19 obtained by collecting and solidifying a molten solder is easily removed from the mold 10, and a surface of the solidified solder sample 19 is smoothened. As the material having low solidability, a material containing, as a main component, any of steel, stainless, nichrome, aluminum, chromium, titanium and ceramics can be used. Among them, particularly, since steel, stainless, and titanium are a material having great corrosion resistance to a solder and having the high heat releasing ability, they solidify a molten solder at a uniform solidification rate, leading to a uniform solidified tissue.

As a structural material for the mold 10, a material of suitable quality may be selected in view of a kind, characteristic and a temperature of a molten metal and, further, contamination·corrosion due to a molten metal, the material cost and the like. According to the experimental result by the present inventor, when a molten metal is a solder, stainless such as SUS304 and SUS316 is preferable.

A plate thickness of the mold 10 must be such that heat of the mold 10 itself is rapidly released in order to release heat of a molten solder rapidly and uniformly, that is, solidify a molten solder by rapid cooling. In addition, when the mold 10 is immersed into a molten solder, a molten solder is adhered and solidified due to a low temperature of the mold 10. In order that a solder is not solidified in a molten solder, the mold 10 must be rapidly heated. From these things, it is desirable that a plate thickness of the mold 10 is smaller for rapid cooling and rapid heating.

FIG. 7A is a view showing a relationship between a plate thickness of the lower mold 11 and the upper mold 12 and the content of Pb which is an impurity in the solder sample 19. In this experiment, a standard solder having the Pb content of 800 ppm was used.

As shown in FIG. 7A, little difference is seen in a measured value of the Pb content by energy dispersive fluorescent X-ray analysis, at a plate thickness of the lower mold 11 and the upper mold 12 of 1, 2 and 5 mm, and the Pb content was detected with high accuracy (800 ppm±30 ppm).

However, when a plate thickness was 10 mm, a white superficial layer was generated on a back surface of the solder sample 19, symptom indicating that a solidification rate is slower than that at a surface of the solder sample 19 began to appear, the Pb content was detected to be 750 mm, and an error was seen in data. And, when a plate thickness of the lower mold 11 and the upper mold 12 was 10 mm, a time until cooling and solidification of a molten solder, which was 2-fold or longer that at a plate thickness of 2 mm, was necessary.

Further, when a plate thickness of the lower mold 11 and the upper mold 12 was increased to 13 mm, a whole back surface of the solder sample 19 became a white surface layer, the content of Pb was detected to be 650 ppm, and an error in data became great.

Therefore, it is necessary that a plate thickness of the lower mold 11 and the upper mold 12 is not greater than 5 mm.

Conversely, when a plate thickness of the lower mold 11 and the upper mold 12 is too small, a mechanical strength of the lower mold 11 and the upper mold 12 is reduced, and the mold is distorted when roughly handled. As shown in FIG. 7B, when a plate thickness of the lower mold 11 and the upper mold 12 is 1 mm, application of a great force deformed the mold, but the mold could be used when carefully handled. In addition, when a plate thickness of the lower mold 11 and the upper mold 12 was 2 mm, the mold was not deformed at normal handling, giving no influence on use.

Further, when repeatedly immersed in a molten solder at 255° C., a possibility of distortion due to a heat cycle is increased. Therefore, it is necessary that a plate thickness of the lower mold 11 and the upper mold 12 is not smaller than 1 mm.

Hence, a plate thickness of the lower mold 11 and the upper mold 12 is suitably 1 to 5 mm. Particularly, in a range of 2 to 5 mm, uniform distribution of impurities and a mechanical strength were stable. Since a time until a molten solder is cooled and solidified is shorter at a smaller plate thickness, a plate thickness was most convenient at 2 mm.

In addition, to describe in terms of a thickness of the mold 10, the thickness is a sum of plate thicknesses of the lower mold 11 and the upper mold 12 and a thickness of the sample collection space 15, that is, a thickness which is 2 to 10 mm plus a thickness of the sample collection space 15.

In addition, as already described, since a size of a planar shape of the sample collection space 15 of the mold 10 is not smaller than 10 mm as expressed by a diameter, a shape of the mold 10 in a planar direction is also determined by a sample bed of an energy dispersive fluorescent X-ray analysis apparatus, and a planer surface having a diameter of not smaller than 10 mm is necessary.

Therefore, a diameter of the collection part 13 of the lower mold 11 is set to be 15 to 30 mm and, further, a thickness from the collection part 13 to an outer periphery of the lower mold 11 is set to be 1 to 5 mm based on the same consideration as that of a plate thickness of the mold 10, for increasing release of heat from the mold 10, and increasing and uniformizing a solidification rate of a solder.

Like this, since the sample collection space 15 is a thin space of 0.3 to 1.5 mm, and the mold 10 surrounding the sample collection space 15 has a thickness of 1 to 5 mm, heat is released rapidly. Therefore, a solidification rate of a solder is uniform and rapid, and a sample 19 in which impurities are uniformly dispersed due to solidification by rapid cooling can be produced rapidly.

B. Process for Producing Solder Sample from Molten Solder

Figure 8:
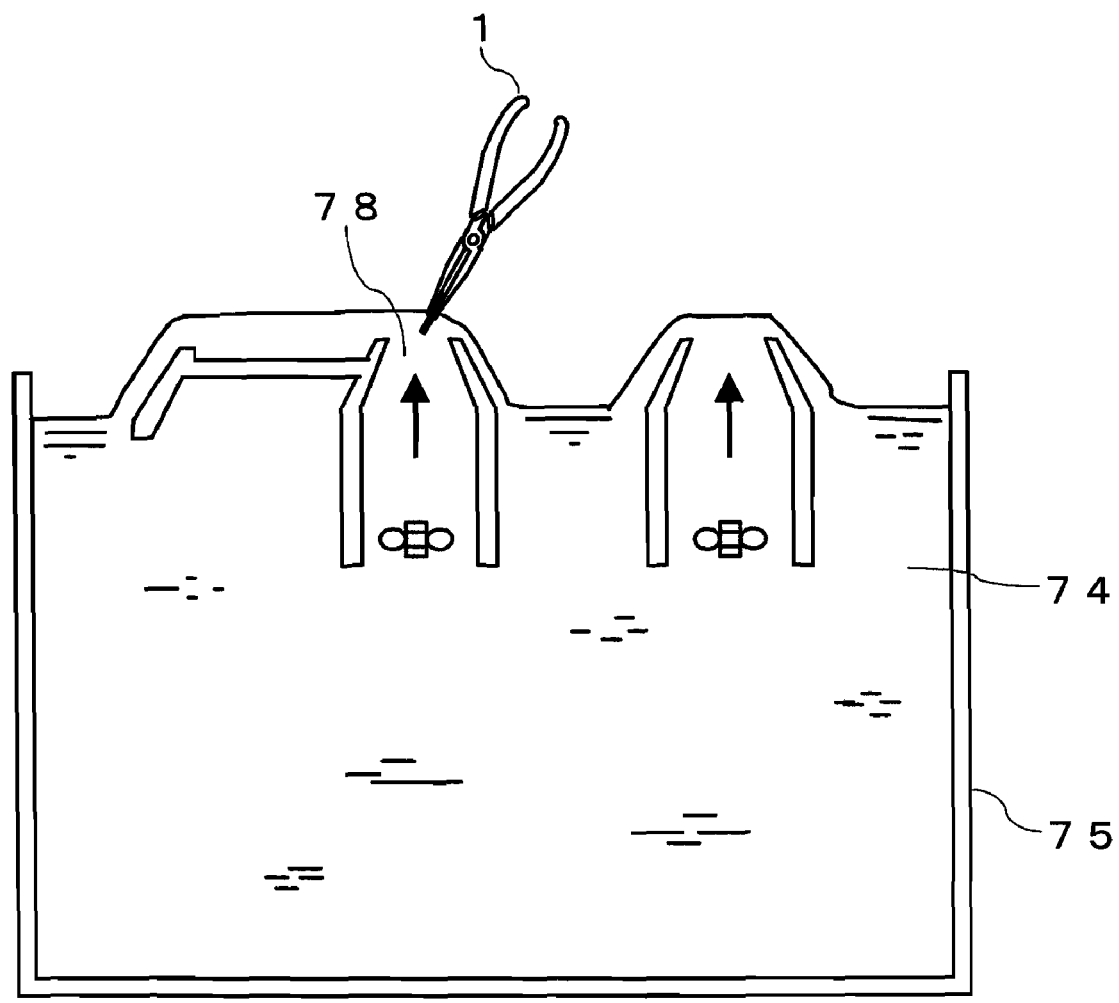
[FIG. 8] A schematic view of collection of a solder sample with a sample production device in accordance with an aspect 1 of the present invention, in a flow soldering apparatus.
Figure 9:
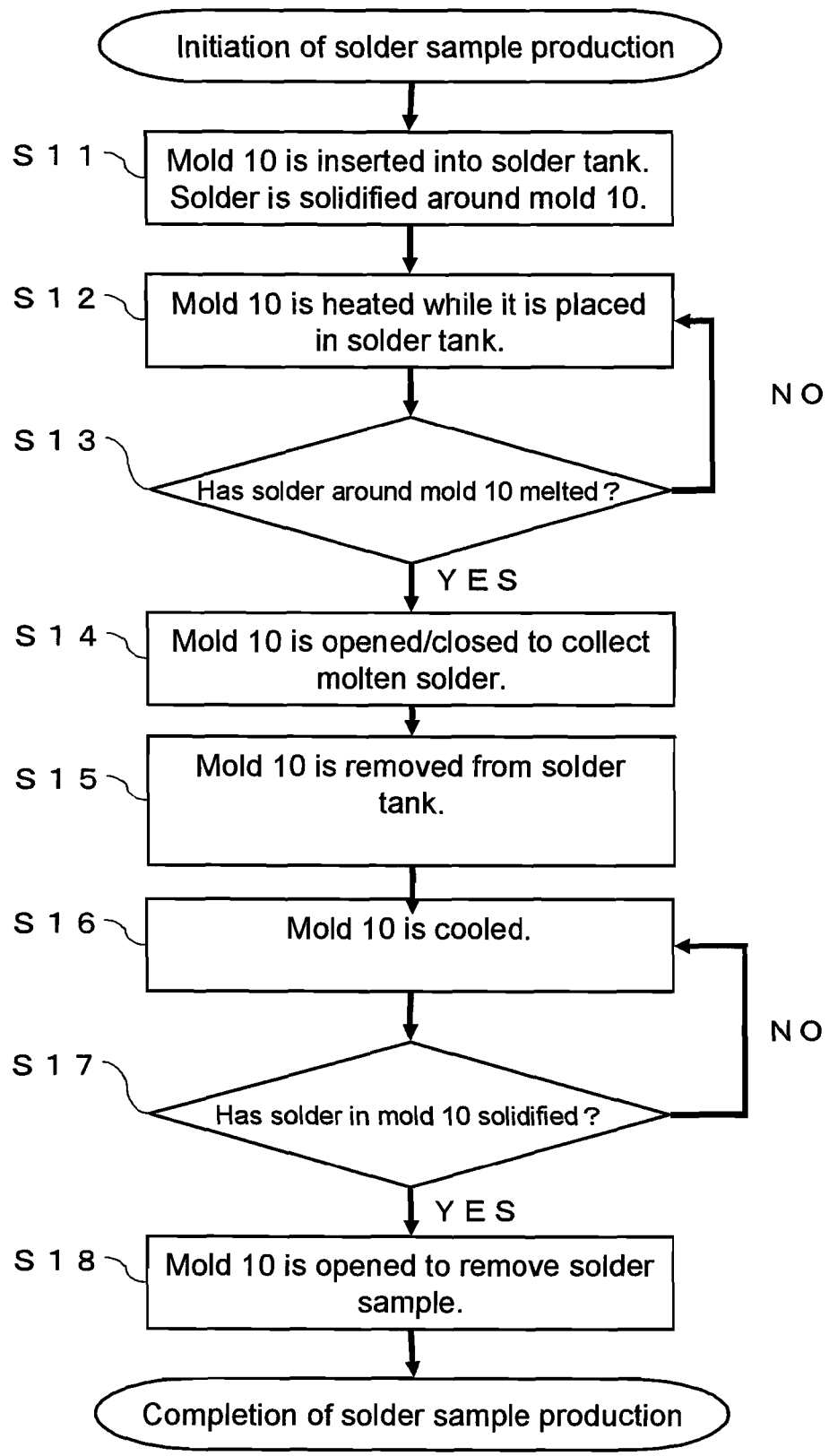
[FIG. 9] A flow chart of collection of a solder sample with a sample production device in accordance with an aspect 1 of the present invention, in a flow soldering apparatus.

FIG. 8 shows one example in which a solder sample 19 is collected from a molten solder using the sample production device 1 of the present invention. FIG. 8 shows an example in which, in a flow soldering step, a mold 10 of the sample production device 1 is immersed in a molten solder 74, which has been melted with a secondary jet 78, in a solder tank 75, thereby, a solder sample 19 for analysis is produced. In addition, a flow chart when a solder sample 19 is collected with a sample production device 1, in a flow soldering step, is shown in FIG. 9. Using FIG. 1, FIG. 2, FIG. 8 and FIG. 9, a method of collecting a solder sample 19 in accordance with an aspect 1 will be explained.

First, the sample production device 1 in the closed state as shown in FIG. 2 is immersed into a molten solder 74 in a solder tank 75, so that the mold 10, and up to rotation arm transmission parts 16a and 17a near the mold 10 are immersed therein. Thereupon, since the sample production device 1 is at a normal temperature (about 25° C.), when immersed into a molten solder at 255° C., a solder is instantly solidified around the mold 10, and rotation arm transmission parts 16a and 17a of the sample production device 1 (S11). For this reason, it becomes impossible instantly to opening/closing-operate the mold 10. However, since the mold 10 has a thin wall, that is, has a small volume, it is rapidly heated and its temperature approaches a temperature (255° C.) of a molten solder, immediately returning a solder, which has been solidified, surrounding the mold 10 to a molten solder.

Although rotation arm transmission parts 16a and 17a are not rapidly heated, since a gap between the rotation arm transmission part 16a and the rotation arm transmission part 17a is not smaller than 4 mm, the rotation arm transmission part 16a and the rotation arm transmission part 17a are not connected to prevent an operation of opening/closing the mold 10.

Until a temperature of the mold 10 approaches a temperature of a molten solder, and a solder solidified around the mold 10 is returned to a molten solder, the mold 10 is heated while it is immersed in a molten solder 74 in a solder tank 75 (S12). After a solder around the mold 10 is melted and returned to a molten solder (S13), since the mold 10 is opened as shown in FIG. 1, an acting force is inputted into the rotation arm acting force inputting part 16b and the rotation arm acting force inputting part 17b, to open the mold 10 in a molten solder 74. Then, an acting force is inputted into the rotation arm acting force inputting part 16b and the rotation arm acting force inputting part 17b to close the mold 10 as shown in FIG. 2, thereby, a molten solder 74 is collected into the sample collection space 15 in a solder tank 75 (S14). Thereupon, a molten solder collected in the collection part 13 is given a pressure with the pushing out part 14, and a molten solder 74 exceeding a volume of the sample collection space 15 is pushed out to the outside of the collection part 13.

Then, the sample production device 1 is removed from the molten solder 74 in the solder tank 75 (S15), and the mold 10 is cooled in the air for 20 to 60 seconds (S16). When the molten solder collected in the sample collection space 15 is solidified by cooling to become a solder sample 19 (S17), in order to remove the solder sample 19 from the mold 10, an acting force for moving the rotation arm acting force inputting part 16b and the rotation arm acting force inputting part 17b away from each other is inputted into both rotation arm acting force inputting parts, thereby, converting the sample production device 1 in the state where the mold 10 is closed as shown in FIG. 2 into the sample production device 1 in the state where the mold 10 is opened as shown in FIG. 1, and the solder sample 19 is removed from the collection part 13 of the lower mold 11 (S18). This flow can complete the solder sample 19.

Since the mold 10 uses a material having low solderability such as stainless, a solder is not adhered to the mold 10, a solidified solder sample 19 can be easily removed, and a sample is obtained in conformity with the mold. That is, since a flat mold is used, a surface of the solder sample 19 is also flat.

Therefore, the solder sample 19 after removal can be immediately subjected to an energy dispersive fluorescent X-ray analysis apparatus without abrasion to analyze components.

According to the sample production process of the present invention, since when the sample production device 1 is removed from the molten solder 74 in the solder tank 75, a solder material has already begun to solidify in the interior of the sample collection space 15, and the solder sample 19 begins to be formed, it becomes possible to cool the mold 10 to a room temperature after removal of the sample production device 1, remove the solder sample 19 from the mold 10, and immediately perform energy dispersive fluorescent X-ray analysis. That is, a necessary time for producing the solder sample 19 from collection of the solder sample 19 to analysis of the sample can be considerably shortened.

In addition, according to the sample production process of the present invention, since a solidification rate of the solder sample 19 is uniform, impurities in the solder are uniformly dispersed, and the content of impurities can be analyzed with high accuracy.

Then, comparison of a sample production time and analysis accuracy of the Pb content between the present sample production process and the previous sample production process, when the molten solder 74 in the solder tank 75 is collected to produce a solder sample according to both processes, will be explained.

One example of Examples of the present invention will be shown below, but the present invention is not limited by adopted conditions.

The sample production process of the present invention is a process of collecting a molten solder 74 with the sample production device 1 shown in FIG. 1 provided with a mold 10 having a circular sample collection space 15 having a diameter of 20 mm and a thickness of 0.5 mm shown in FIG. 4, and rapidly cooling the solder to produce a solidified solder sample 19.

The previous sample production process is a process of collecting a molten solder 74 with a crucible 94 as shown in FIG. 23, and flattening the solder on a metal plate 95 to produce a thin plate-solder sample 96.

As for a sample production time, it was confirmed that production of a solder sample 96 from collection of molten solder 74 needs about 60 seconds in the previous process, while a solder sample 19 can be produced in about 20 to 40 seconds in the present process.

As for analysis accuracy of the content of Pb which is an impurity, each five of solder samples 19 and 96 were produced form a molten solder 74 containing 800 ppm of Pb by the present process and the previous process, respectively, and values of the Pb content measured by energy dispersive fluorescent X-ray analysis were compared. Results are shown in FIG. 10.

Figure 10:
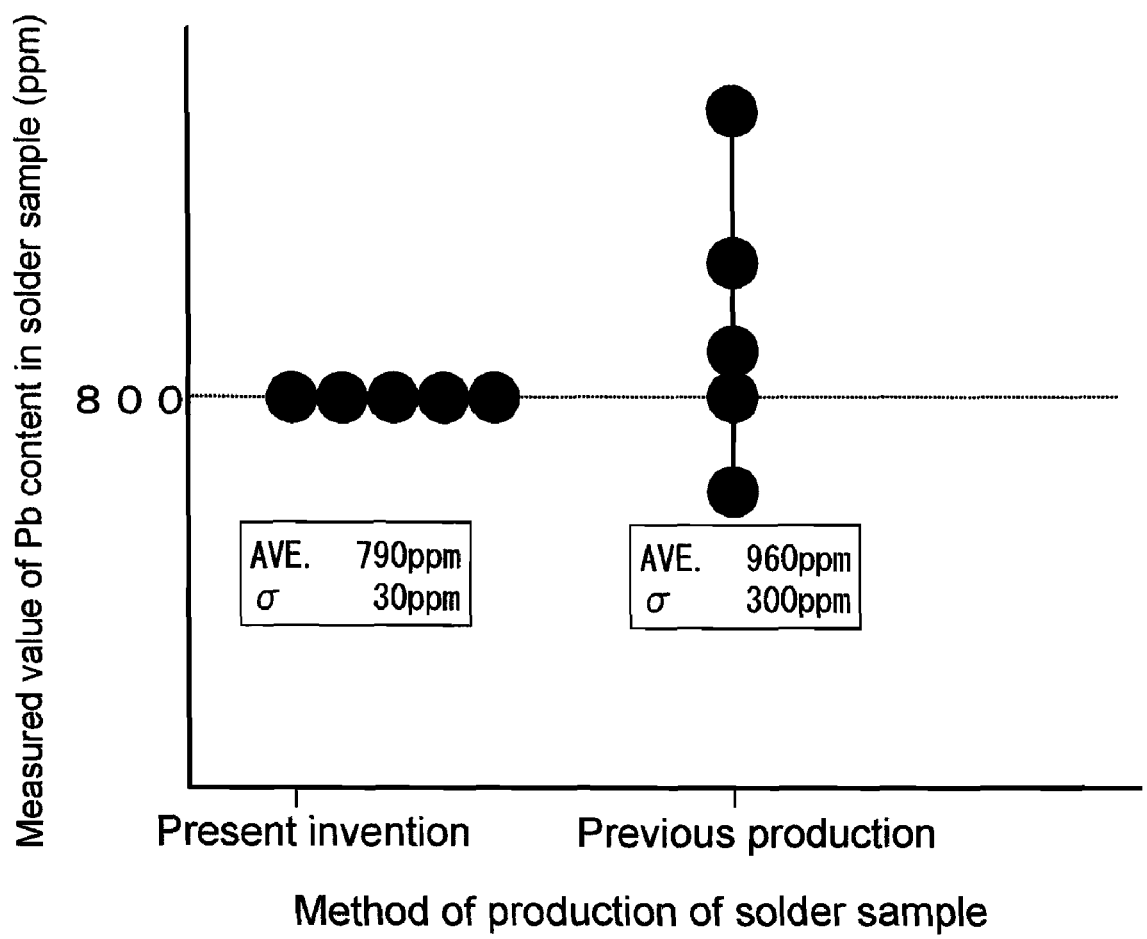
[FIG. 10] A view of comparison of the Pb content of a solder sample between a sample production process in accordance with an aspect 1 of the present invention, and the previous sample production process.

As shown in FIG. 10, in the analysis result of the Pb amount of the solder sample 96 produced by the previous process, an average value was 960 ppm, and a standard deviation ($\sigma$) was 300 ppm, thus, there was a large error in data, and a scatter was large. On the other hand, in the analysis result of the Pb amount of the solder sample 19 produced by the present process, an absolute value of the Pb content was approximately the same as the Pb content of a solder material, and a scatter in the analysis result was small as being 1/10 a scatter of the previous process (average value 790 ppm, standard deviation $\sigma$ 30 ppm), thus, it was found out that analysis with high accuracy is possible.

According to such the construction, it becomes possible to immerse a mold in a molten solder to collect a solder, thereby, producing a thin plate-like solder sample, by adopting construction of fixation of a mold which has low solderability and is thin plate-type, to a tip of an opening/closing operation part, a solder sample for energy dispersive fluorescent X-ray analysis can be easily and rapidly collected, and a solder sample for analysis by which the content can be measured with high accuracy, in response to the content limit of Certain Hazardous Substances(lead, mercury, cadmium, hexavalent chromium) of RoHS Directive, can be produced.

In the present aspect, although the aspect has been explained referring to measurement of the content of lead contained in the solder sample 19, since impurities are uniformly dispersed in the solder sample 19 produced by the present aspect due to rapid cooling, the content can be similarly measured with high accuracy also in measurement of other impurities such as mercury, cadmium, and hexavalent chromium.

Therefore, in the present aspect, the solder sample 19 by which the content of impurities contained in the solder sample 19 can be measured with high accuracy, can be produced.

In the present aspect, although the mold was immersed into the molten solder to produce the solder sample for which impurities contained in a solder are analyzed, the mold may be immersed into a molten metal other than a solder to produce a metal sample for which impurities contained in the metal are analyzed. Thereupon, since a melting point and a solidification point of the metal sample are higher as compared with those of a solder, when a molten metal is collected with the sample production device of the present invention, and the mold is removed from the molten metal, a solidified metal sample can be produced in a few seconds by rapidly cooling a molten metal.

In the present aspect, although the concave part 14$m$ for marking was provided at the pushing out part 14 of the upper mold 12 for recognizing a back side of the solder sample 19, a convex part for marking may be provided. Thereupon, a concave marking is formed in the solder sample 19 and, even when the solder sample 19 is placed with a back side being an underside, a marking is not destructed.

In the present aspect, although the concave part 14$m$ for marking was provided at the pushing out part 14 of the upper mold 12 for recognizing a back side of the solder sample 19, a convex part for marking may be provided at the collection part 13 of the lower mold 11 for recognizing a surface side of the solder sample 19. Thereupon, a concave part for marking is formed in the solder sample 19, and a marking is not destructed even at measurement by energy dispersive fluorescent X-ray analysis for which the solder sample 19 is placed with a surface side being an underside.

In the present aspect, although the circular concave part 14$m$ for marking was provided for recognizing a back side of the solder sample 19, a concave part or a convex part for marking may be provided using a letter such as a numeral and an alphabet. For example, when the impurities content of a plurality of solder tanks is controlled, a letter for marking is decided for each solder tank, solder tanks can be discriminated with a marking letter assigned to the solder sample 19, and quality control can be performed for every solder tank.

In addition, although after the mold 10 of the sample production device was removed from a molten solder, the mold 10 was cooled in the air, the mold may be cooled with a cloth containing water. In this case, a cooling time requiring about 20 to 40 seconds for cooling in the air can be reduced to ½ as being about 10 to 20 seconds.

In the present aspect, although a gap between the rotation arm transmission part 16$a$ and the rotation arm transmission part 17$a$ at an opening/closing operation part was set to be a thickness of the mold, a gap between the rotation arm transmission part 16$a$ and the rotation arm transmission part 17$a$ may be not smaller than a thickness of the mold as shown in FIG. 11 and FIG. 12. In this case, even when the mold 10 is immersed into a molten solder, and the mold is closed as shown in FIG. 1, a possibility that solders solidified around rotation arm transmission parts 26$a$ and 27$a$ are connected to prevent an opening/closing operation of the mold 10 of the sample production device 2 is further lowered.

In the present aspect, although the opening/closing operation part of the mold had a pincher shape, the sample production device 3 may be constructed such that the operation part has a plier shape, in which a position of the rotation supporting point 38 can be moved to different positions of supporting points 38$a$ and 38$b$ on the rotation arm 36 as shown in FIG. 13 and FIG. 14. In this case, by moving a supporting point from 38$a$ in FIG. 13A to 38$b$ in FIG. 13B, a gap between rotation arms 36 and 37, and a gap between the lower mold 11 and the upper mold 12 can be widened. This is effective when the collection part 13 of the lower mold 11 and the pushing out part 14 of the upper mold 12 are cared, for example, cleaned.

Figure 15:
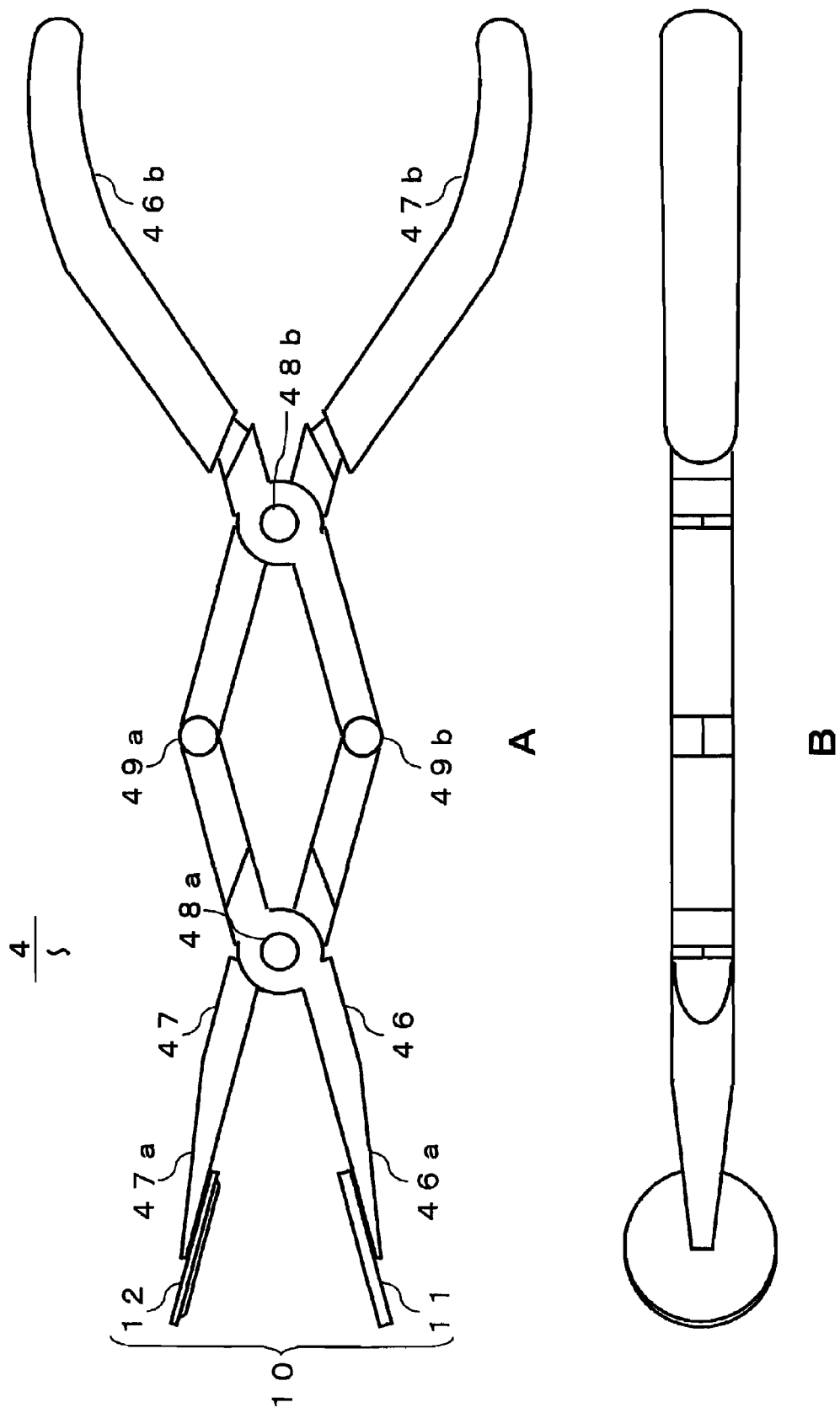
[FIG. 15] A structural view when a mold of a sample production device 4 in accordance with an aspect 1 of the present invention is opened; A: front view, B: side view.
Figure 16:
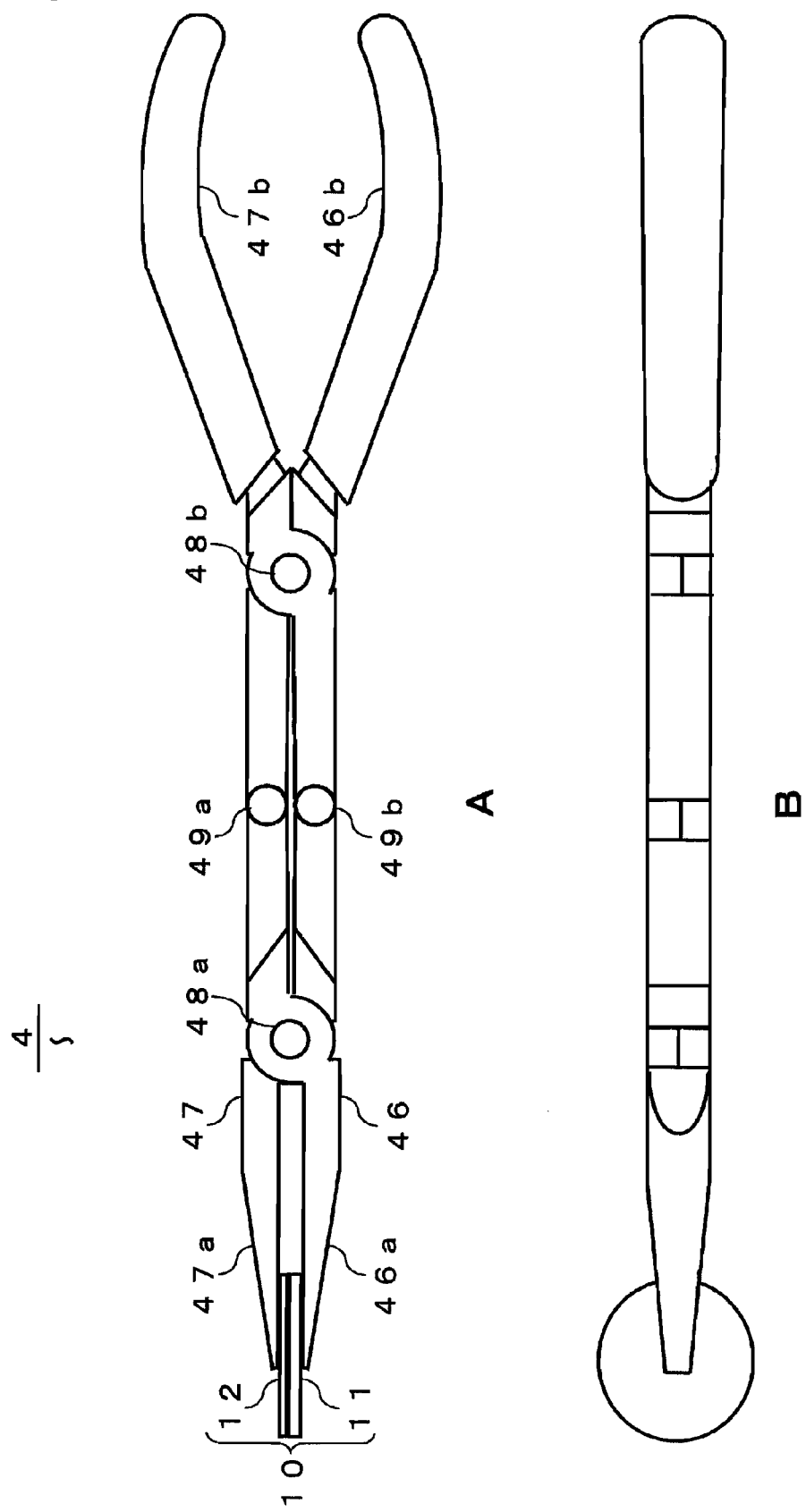
[FIG. 16] A structural view when a mold of a sample production device 4 in accordance with an aspect 1 of the present invention is closed; A: front view, B: side view.

In the present aspect, although the opening/closing operation part of the mold had a pincher shape equipped with one pair of rotation arms, the sample production device 4 may be constructed such that the operation part has a magic hand shape, in which an acting force inputted into rotation arm acting force inputting parts 46$b$ and 47$b$ is transmitted to rotation arm transmission parts 46$a$ and 46$b$ via rotation arm transmission supporting points 49$a$ and 49$b$ as shown in FIG. 15 and FIG. 16. In this case, even when a solder tank from which the solder sample 19 is to be collected is far from a person who collects a sample, rotation arms 46 and 47 extend so that the mold 10 can reach the solder tank.

Figure 18:
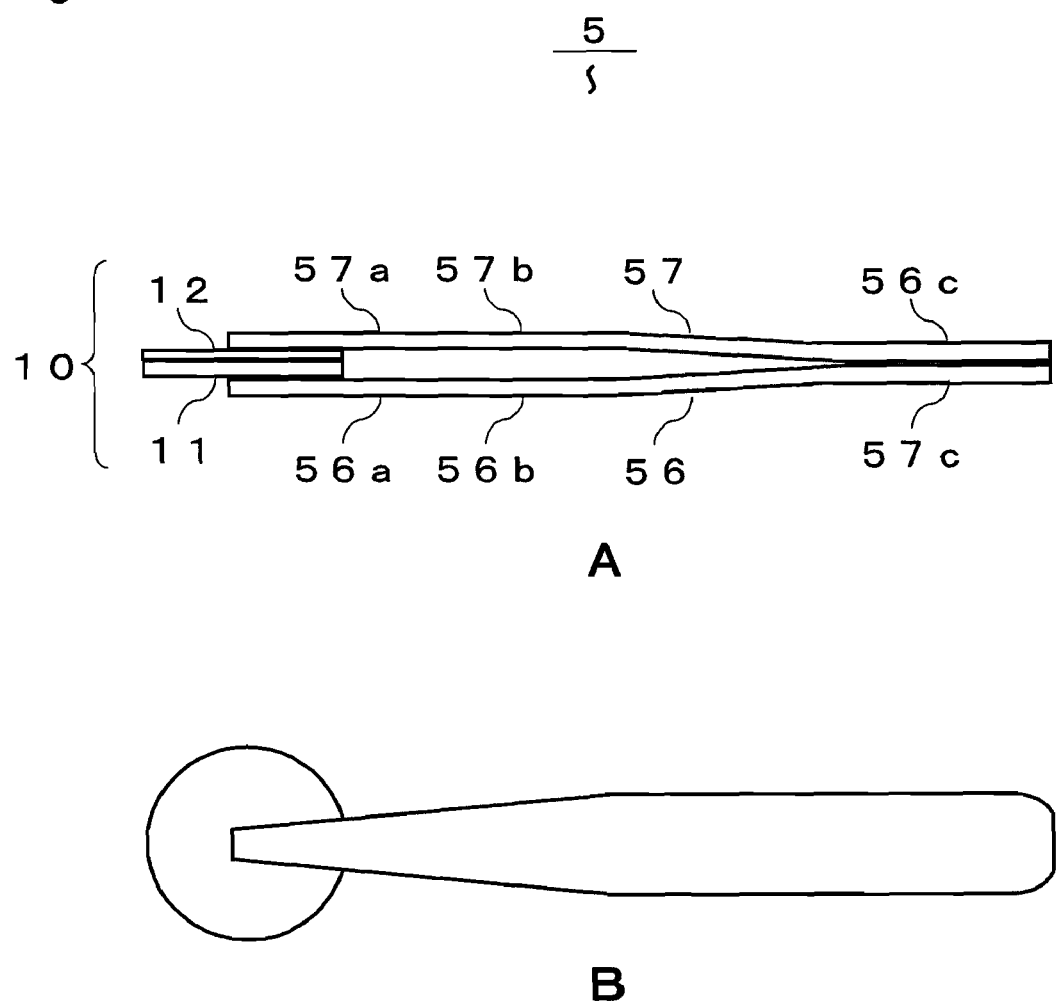
[FIG. 18] A structural view when a mold of a sample production device 5 in accordance with an aspect 1 of the present invention is closed; A: front view, B: side view.

In the present aspect, although the opening/closing operation part of the mold had a pincher shape equipped with one pair of rotation arms, the sample production device 5 may be constructed such that the operation part has a pincette shape, in which one pair of arms 56 and 57 are connected with an arm connecting part 56$c$ and an arm connecting part 57$c$, as shown in FIG. 17 and FIG. 18. In this case, the lower mold 11 is fixed to an arm transmission part 56$a$, and the upper mold 12 is fixed to an arm transmission part 57$a$ as shown in FIG. 17 and FIG. 18, and the mold 10 is usually in the opened state as shown in FIG. 17. For opening and closing the mold, an acting force for bringing arms 56 and 57 closer to each other is inputted into arm acting force inputting parts 56$b$ and 57$b$, thereby, the mold can be closed. And, by relaxing an acting force inputted into arm acting force inputting parts 56$b$ and 57$b$, the mold 10 can be opened.

In the method of collecting a solder sample 19 with the sample production device 5, the mold 10 in the opened state as shown in FIG. 17 is immersed into the molten solder 75 in the solder tank 75, and an acting force is inputted so as to bring one pair of arms 56 and 57 closer to each other, to close the mold 10 as shown in FIG. 18. The molten solder 75 is collected, the mold is cooled in the air for 20 to 30 seconds to solidify the molten solder 74, thereafter, an acting force inputted into arms 56 and 57 is weakened to bring the sample production device 5 into the state where the mold 10 is opened as shown in FIG. 18, and the solder sample 19 is removed.

Figure 19:
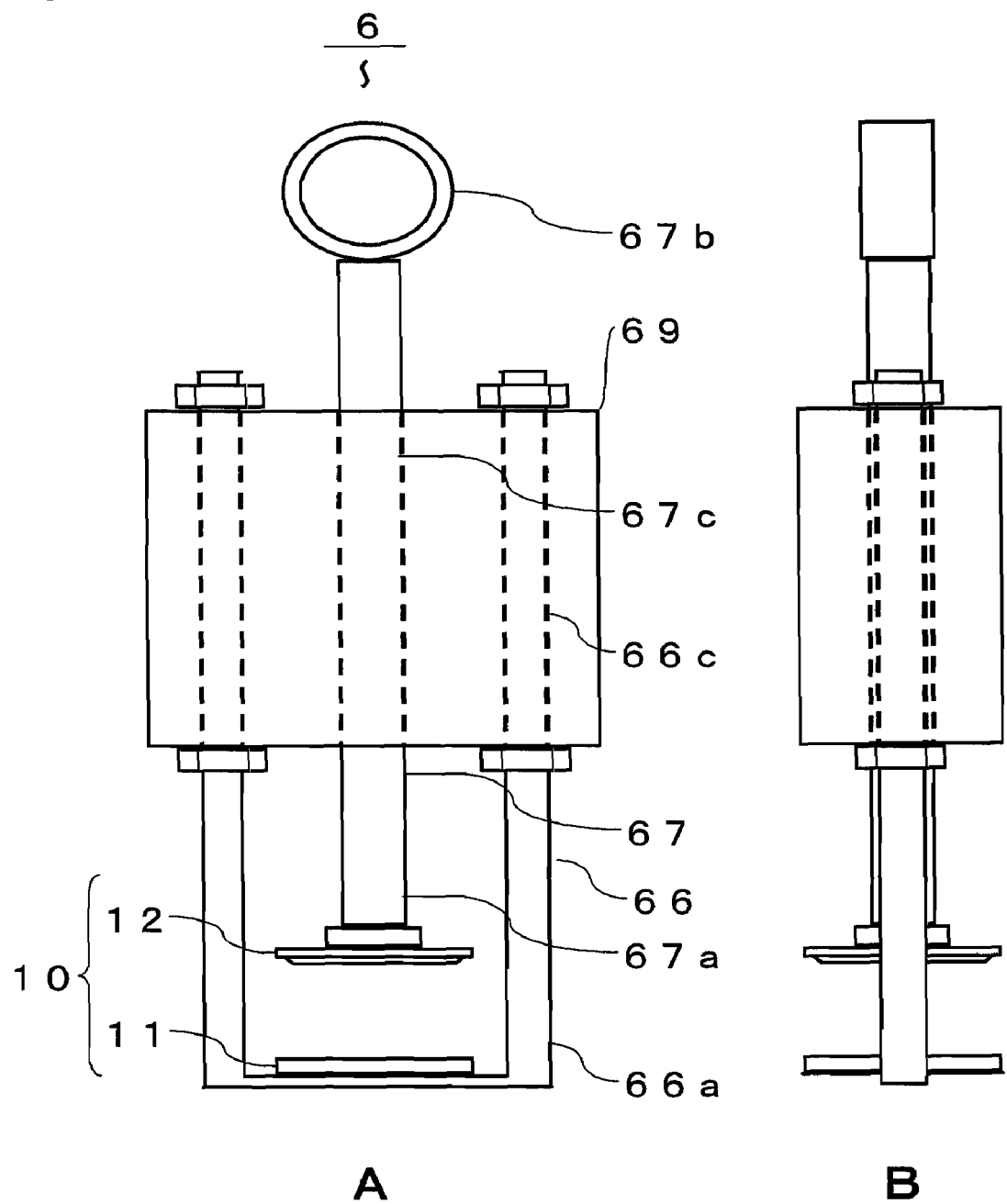
[FIG. 19] A structural view when a mold of a sample production device 6 in accordance with accordance with an aspect 1 of the present invention is opened; A: front view; B: side view.
Figure 20:
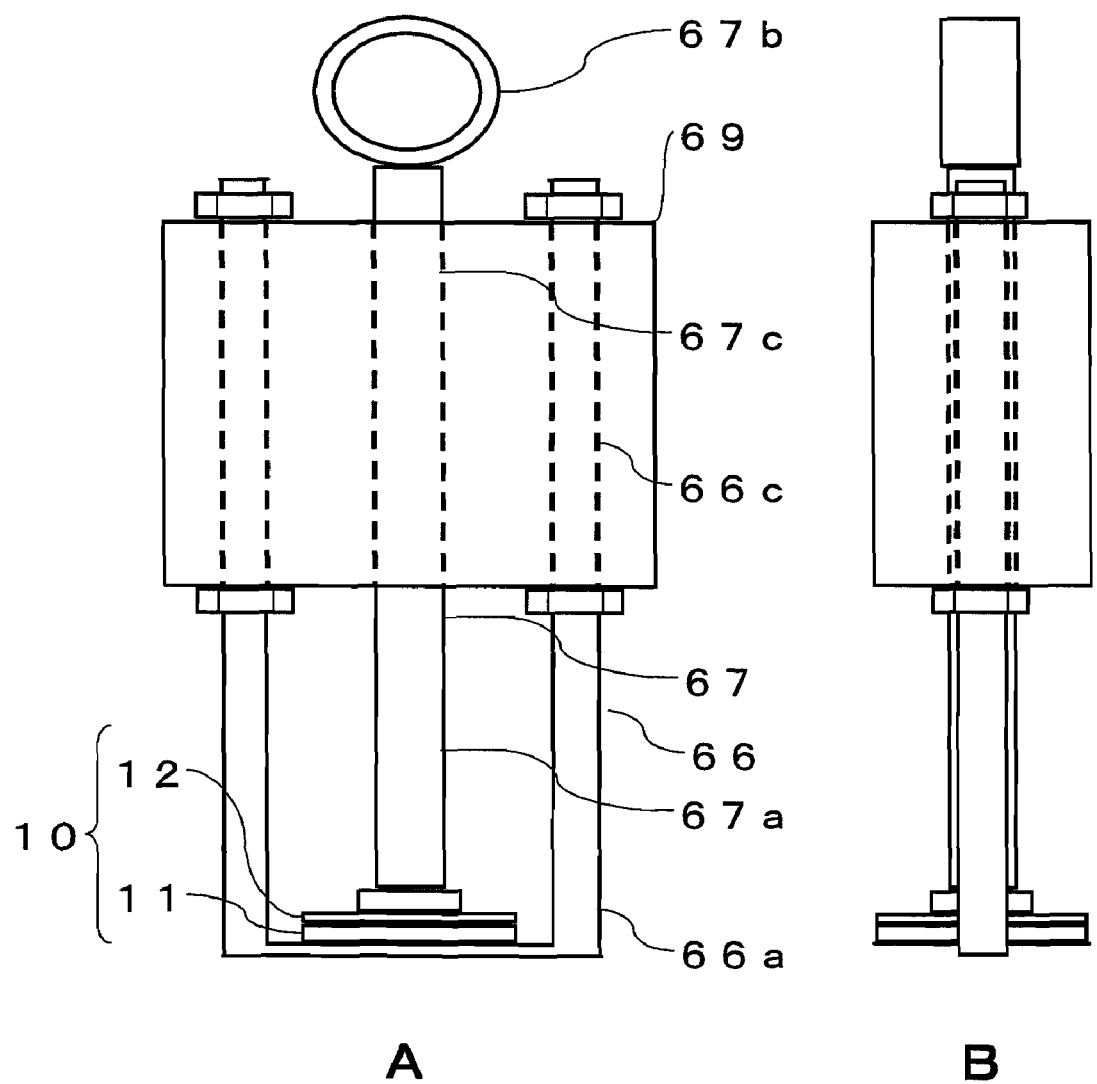
[FIG. 20] A structural view when a mold of a sample production device 6 in accordance with an aspect 1 of the present invention is closed; A: front view, B: side view.
Figure 22:
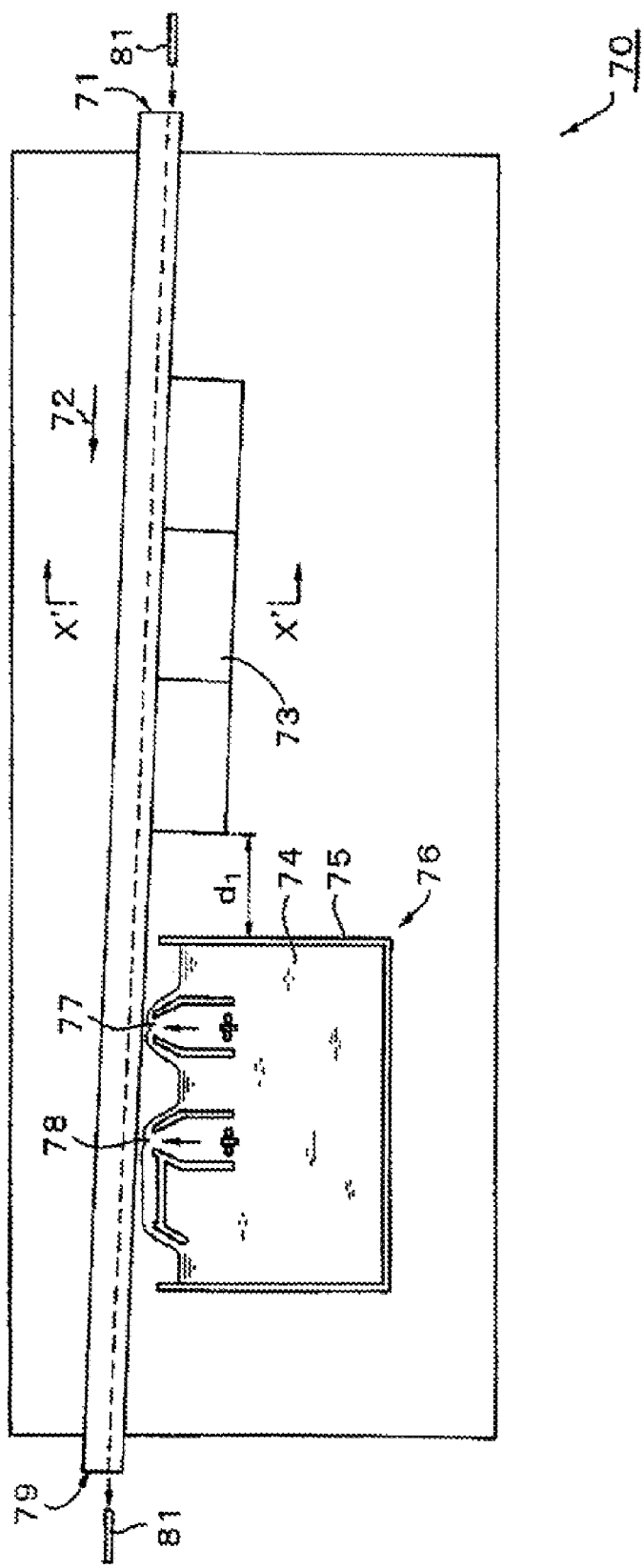
[FIG. 22] A schematic cross-sectional view of the previous flow soldering apparatus.
Figure 25:
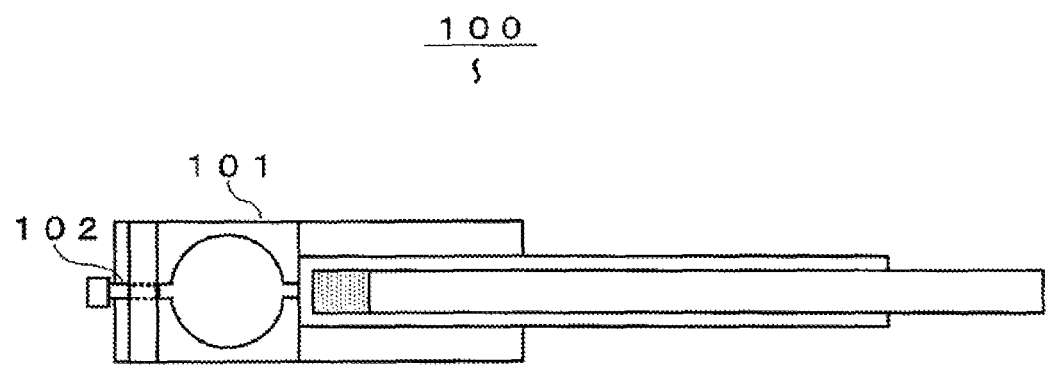
[FIG. 25] A structural view of the previous sample production device.

In the present aspect, although the opening/closing operation part of the mold had a pincher shape equipped with one pair of rotation arms, the lower mold 11 may be fixed to an arm transmission part 66$a$ around a horizontal line of a U letter of an arm 66, and an arm connecting part 66$c$ around two vertical lines of a U letter of an arm 66 is secured with an arm securing part 69 as shown in FIG. 19 and FIG. 20. And, an arm 67 is such that the upper mold 12 is fixed to a tip of an arm transmission part 67*a*, and an arm acting force inputting part 67*b* is ring-like so that an acting force is inputted by placing a finger therein. The arm 67 is penetrated through a long pore in the arm securing part 69, and can be slided in a direction vertical to the mold 10. By inputting an acting force into an arm acting force inputting part 67*b* in the state where the mold 10 is opened as shown in FIG. 19, the mold 10 can be brought into the closed state as shown in FIG. 20.

(Aspect 2)

In the aspect 1, by making the sample production device with a material having low solderability, and optimizing a gap dimension and a shape of the rotation arm transmission part, it enabled to produce a solder sample for analysis for which the content of impurities can be easily and rapidly measured with high accuracy.

In the aspect 2, a sample production device will be explained, in which solderability is further reduced, and a surface of the sample production device is nitriding-treated in order to prevent adhesion of a solder when the sample production device is immersed into a molten solder.

FIG. 21 is a fundamental structural view of a sample production device 7 of the aspect 2 of the present invention. In FIG. 21, regarding the same component as that in FIG. 1, the same symbol is used, and explanation is omitted.

In FIG. 21, the sample production device 7 has the same dimension, shape, and stainless in a fundamental structure as those of the sample production device 1 of the aspect 1. The sample production device 7 is such that a surface of stainless of the sample production device 7 is nitriding-treated to form a nitriding-treated layer 20 on a whole surface of stainless. In FIG. 21, the nitriding-treated layer 20 is expressed with black.

The nitriding-treated layer 20 is a CrN layer, that is, a chromium nitride alloy layer formed on a surface of stainless when stainless which is a structural material of a lower mold 11, an upper mold 12, and rotation arms 16 and 17 is nitriding-treated. Since the CrN layer is diffused to a depth of 20 to 80 μm from a surface of stainless, change in a structural dimension of a stainless steel is only about 1 to 5 μm, and a change in a dimension due to the CrN layer does not influence on fitting of the lower mold 11 and the upper mold 12. In addition, since a surface roughness is hardly changed from that before treatment, and does not hardly change a surface roughness of the collection part 13 of the lower mold 11 and the pushing out part 14 of the upper mold 12, smoothness of a measurement surface of energy dispersive fluorescent X-ray analysis which is a surface of a solder is not influenced. That is, the same solder sample 19 as that of the sample production device 1 of the aspect 1 can be collected.

In addition, the nitriding-treated layer 20 has the characteristic that it enhances a Vickers hardness of stainless from around 200 to a carbide level of 600 to 1500, and improves abrasion resistance and, at the same time, reduces solderability with a molten solder.

Then, nitriding treatment will be explained. Nitriding treatment is one of diffusion treating methods with a vacuum furnace, and is treatment of disposing a subject to be nitrided, a sample production device before nitriding treatment in the present invention, in a high vacuum furnace, supplying a nitriding promotion gas containing $NH_3$, that is, ammonia as a main component into the furnace, and diffusing this in a material surface of stainless. A treating temperature is between 500° C. to 540° C., and a soaking period at that treating temperature is about 5 hours.

The sample production device 7 equipped with the nitriding-treated layer 20 by nitriding treatment on a surface of stainless of the sample production device 1 has more reduced solderability, and adhesion of a solder due to solidification can be more reduced when the lower mold 11 and the upper mold 12 of the sample production device 7 are immersed into a molten solder.

With such the construction, by adopting the construction that solderability is lower, and a thin-plate mold is fixed to a tip of the opening/closing operation part, it becomes possible to immerse a mold into a molten solder to collect a solder, thereby, producing a thin plate solder sample, a solder sample for energy dispersive fluorescent X-ray analysis can be easily and rapidly collected, and a solder sample for analysis for which the content can be measured with high accuracy, regarding a content limit of Certain Hazardous Substances (lead, mercury, cadmium, hexavalent chromium) of RoHS Directive, can be produced.

In the present aspect, although a structural material of the sample production device was a stainless steel, a material containing not less than 5% of Cr may be used. When not less than 5% of Cr is contained, a nitriding-treated layer can be provided by nitriding treatment, and solderability can be reduced. Thereby, even when the sample production device is immersed in a molten solder, a solder is not adhered to the sample production device to prevent an opening/closing operation of the mold.

In the present aspect, although a nitriding-treated layer was provided in the sample production device 1 of the aspect 1, a nitriding-treated layer may be provided in any of the sample production device 2, the sample production device 3, the sample production device 4 and the sample production device 5. Like provision of the nitriding-treated layer in the sample production device 1, solderability is reduced, and a molten solder or a molten metal can be prevented from adhering to the sample production device to reduce operability of the sample production device.

INDUSTRIAL APPLICABILITY

The sample production device and the sample production process of the present invention enable to easily and rapidly collect a sample for analysis for determining the content of impurities contained in a molten metal, particularly a molten solder easily, rapidly and with high accuracy and, at the same time, can measure, with high accuracy, whether four Certain Hazardous Substances (lead, mercury, cadmium, hexavalent chromium) designated by RoHS Directive are contained as impurities or not, thus, the present invention is useful for collecting a sample for analysis used in energy dispersive fluorescent X-ray analysis.

The invention claimed is:

1. A process for producing a solder sample to analyze a Pb content of a molten solder in a solder tank, the method comprising:

a step of immersing a mold in the molten solder, the mold comprising a lower mold having a concave part which can receive the molten solder, and an upper mold having a convex part which fits in the concave part, wherein when the mold is closed so as to insert the convex part in the concave part, a sample collection space is formed between a bottom of the concave part and a lower surface of the convex part, wherein the lower surface of the convex part is a planar surface, and wherein the mold is immersed in the molten solder in the closed state, a step of heating the mold in the molten solder in a solder tank until its temperature approaches a temperature of the molten solder so as to return a solidified solder surrounding the mold to a molten state, a step of opening and closing the mold in a molten metal to collect the molten solder in the sample collection space, a step of removing the mold in the closed state from the molten solder, a step of cooling the mold to solidify the molten solder, and a step of removing a solidified solder sample from the mold for analysis, wherein the sample collection space is a thin space of 0.3 to 1.5 mm, and the mold surrounding the sample collection space has a thickness of 1 to 5 mm.

* * * * *